US010517540B1

(12) United States Patent
Anderson et al.

(10) Patent No.: US 10,517,540 B1
(45) Date of Patent: Dec. 31, 2019

(54) SYSTEMS AND METHODS TO REDUCE DATA AND COMPLEXITY IN NEURAL SIGNAL PROCESSING CHAIN

(71) Applicant: HI LLC, Los Angeles, CA (US)

(72) Inventors: Kristopher Anderson, Santa Monica, CA (US); Randal Koene, San Francisco, CA (US); Antonio H. Lara, Sherman Oaks, CA (US); John W. Stanton, New York, NY (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/252,557

(22) Filed: Jan. 18, 2019

Related U.S. Application Data

(60) Provisional application No. 62/714,997, filed on Aug. 6, 2018.

(51) Int. Cl.
*A61B 5/00* (2006.01)
*A61B 5/04* (2006.01)
*G06F 17/16* (2006.01)
*A61B 5/048* (2006.01)

(52) U.S. Cl.
CPC ........ *A61B 5/7203* (2013.01); *A61B 5/04001* (2013.01); *A61B 5/04004* (2013.01); *A61B 5/048* (2013.01); *A61B 5/04012* (2013.01); *A61B 5/6868* (2013.01); *A61B 5/7221* (2013.01); *G06F 17/16* (2013.01); *A61B 2562/0209* (2013.01)

(58) Field of Classification Search
CPC ..... A61B 5/0476; A61B 5/0478; A61B 5/048; A61B 5/005; A61B 5/0031; A61B 5/04001; A61B 5/04002; A61B 5/04004; A61B 5/04012; A61B 5/04014; A61B 5/04017; A61B 5/0482; A61B 5/0484; A61B 5/72; A61B 5/7203; A61B 5/7207; A61B 5/7228; A61B 5/7232; A61B 5/7253; A61B 5/7257; A61B 5/726; A61B 2562/028; A61B 2562/0285; A61B 2562/04; A61B 2562/043; A61B 2562/046; A61B 2562/06; A61B 2562/064; A61B 2562/066; G06F 17/16
See application file for complete search history.

(56) References Cited

U.S. PATENT DOCUMENTS

| 5,274,832 A | 12/1993 | Khan |
|---|---|---|
| 5,471,627 A | 11/1995 | Means et al. |
| 6,675,187 B1 | 1/2004 | Greenberger |

(Continued)

OTHER PUBLICATIONS

Åström, et al., Wavelet-Based Event Detection in Implantable Cardiac Rhythm Management Devices, IEEE Transactions on Biomedical Engineering, vol. 53, No. 3, Mar. 2006.

(Continued)

*Primary Examiner* — Eun Hwa Kim
(74) *Attorney, Agent, or Firm* — ALG Intellectual Property, LLC

(57) ABSTRACT

Described herein are systems and methods for reducing the size of data payloads delivered to downstream processing from a raw series of biological sensor recordings. In one variation, the system comprises a low-power hardware architecture that combines serially sampled neural signal data with a transformation matrix (TFM) using a novel systolic random-logic-macro (RLM) array.

29 Claims, 13 Drawing Sheets

(56) References Cited

U.S. PATENT DOCUMENTS

| | | | |
|---|---|---|---|
| 6,810,285 | B2 | 10/2004 | Pless et al. |
| 6,901,422 | B1 | 5/2005 | Sazegari |
| 7,043,514 | B1 | 5/2006 | Achlioptas |
| 7,321,915 | B2 | 1/2008 | Lee |
| 7,647,118 | B1 | 1/2010 | Voelkel |
| 9,242,094 | B2 | 1/2016 | Della Santina et al. |
| 10,307,105 | B2 * | 6/2019 | Taulu ................ A61B 5/04 |
| 2004/0106957 | A1 * | 6/2004 | Palreddy ............ A61B 5/0452 607/9 |
| 2007/0022063 | A1 | 1/2007 | Lightowler |
| 2009/0024185 | A1 | 1/2009 | Kulkarni et al. |
| 2009/0287107 | A1 * | 11/2009 | Beck-Nielsen ...... A61B 5/0476 600/544 |
| 2016/0113587 | A1 * | 4/2016 | Kothe ................ A61B 5/7203 600/301 |

OTHER PUBLICATIONS

Belouchrani, et al., A Blind Source Separation Technique Using Second-Order Statistics, IEEE Transactions on Signal Processing, vol. 45, No. 2, Feb. 1997.

Brendel, et al., Demixed Principal Component Analysis.

Cunningham, et al., Dimensionality reduction for large-scale neural recordings, Nature Neuroscience, Advance Online Publication, 2014 Nature America, Inc.

Eichele, et al., Unmixing concurrent EEG-fMRI with parallel independent component analysis, Science Direct, International Journal of Psychophysiology 67, (2008), 222-234.

Farshchi, et al., An Embedded System Architecture for Wireless Neural Recording, IEEE EMBS Conference on Neural Engineering Kohala Coast, Hawaii, USA, May 2-5, 2007.

Gfrerer, et al., Optimization Methods for Sparse Matrix-Vector Multiplication, University of Salzburg, Department of Computer Sciences, Seminar for Computer Science, Prof. Dipl-Ing. Dr. Wolfgang Pree, Summer term 2012.

Harikumar, et al., Dimensionality Reduction Techniques for Processing Epileptic Encephalographic Signals, Biomedical & Pharmacology Journal vol. 8(1), 103-106 (2015).

Heath, et al., Processor-Efficient Sparse Matrix-Vector Multiplication, Science Direct, Department of Computer Science, Virginia Polytechnic Institute and State University Blacksburg, VA 24061-0106, U.S.A.

Hendrickson, et al., An Efficient Parallel Algorithm for Matrix-Vector Multiplication, International Journal of High Speed Computing, Mar. 1995.

Im, et al., Optimizing the Performance of Sparse Matrix-Vector Multiplication, Report No. UCB/CSD-00/1104, Jun. 2000, Computer Science Division (EECS), University of California Berkeley, California 94720.

Jäckel, et al., Applicability of independent component analysis on high-density microelectrode array recordings, J Neurophysiol 108: 334-348, 2012. First published Apr. 4, 2012.

Koyrakh, et al., Data Compression for Implantable Medical Devices, Computers in Cardiology 2008; 35:417-420.

Milovanovic, et al., Designing of Processor-Time Optimal Systolic Arrays for Band Matrix-Vector Multiplication, Computers Math. Applic. vol. 32, No. 2, pp. 21-31, 1996.

Milovanovic, et al., Synthesis of a unidirectional systolic array for matrix-vector multiplication, Science Direct, Faculty of Electronic Engineering, University of Nis, Beogradska 14, 18000 Nis, Serbia and Montenegro.

Mutihac, et al., PCA and ICA Neural Implementations for Source Separation—A Comparative Study, Department of Electricity and Biophysics, University of Bucharest, PO Box MG 11, 76900 Bucharest, Romania.

Olsson III, et al., A Three-Dimensional Neural Recording Microsystem With Implantable Data Compression Circuitry, IEEE Journal of Solid-State Circuits, vol. 40, No. 12, Dec. 2005.

Rodríguez-Pérez, et al., A 330 µW, 64-Channel Neural Recording Sensor with Embedded Spike Feature Extraction and Autocalibration, IEEE Asian Solid-State Circuits Conference, Nov. 10-12, 2014, Kaohsiung, Taiwan.

Shenoy, et al., Cortical Control of Arm Movements: A Dynamical Systems Perspective, Annual Review of Neuroscience. 2013. 36:337-59.

Thorbergsson, et al., Strategies for High-Performance Resource-Efficient Compression of Neural Spike Recordings, PLOS ONE, www.plosone.org, Apr. 2014, vol. 9, Issue 4.

Urquhart, et al., Systolic matrix and vector multiplication methods for signal processing, IEE Proceedings, vol. 131, Pt. F, No. 6, Oct. 1984.

Williamson, et al., Scaling Properties of Dimensionality Reduction for Neural Populations and Network Models, PLOS Computational Biology, Dec. 7, 2016.

* cited by examiner

```
y[0:M-1].ELVALID = true
for r in [0:N-1]:
    reduced = 0.0
    for c in [0:N-1]:
        if W[r,c]!=0.0: if abs(W[r,c]) >= epsilon:
            if x[c].SAMPLEVALID==false:
                y[r].ELVALID=false
                break;
            else:
                reduced += W[r,c]*x[c].value
    y[r].value = reduced
```

FIG. 5A

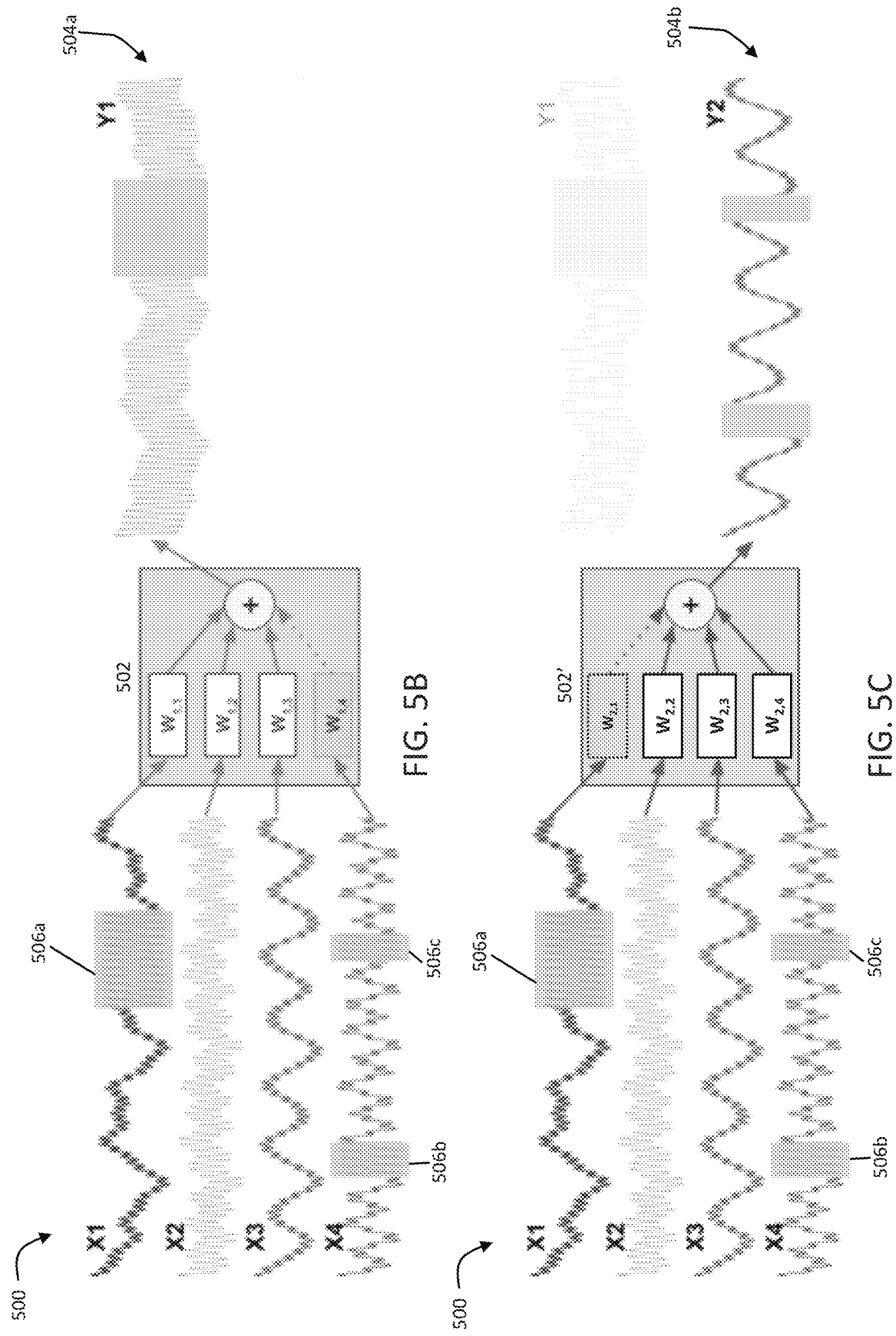

Bipolar reference
[4×5]

$$\begin{bmatrix} 1 & -1 & 0 & 0 & 0 \\ 0 & 1 & -1 & 0 & 0 \\ 0 & 0 & 1 & -1 & 0 \\ 0 & 0 & 0 & 1 & -1 \end{bmatrix}$$

FIG. 6A

Laplacian reference
[3×5]

$$\begin{bmatrix} 1 & -2 & 1 & 0 & 0 \\ 0 & 1 & -2 & 1 & 0 \\ 0 & 0 & 1 & -2 & 1 \end{bmatrix}$$

FIG. 6B

Global average reference
[5×5]

$$\begin{bmatrix} 0.8 & -0.2 & -0.2 & -0.2 & -0.2 \\ -0.2 & 0.8 & -0.2 & -0.2 & -0.2 \\ -0.2 & -0.2 & 0.8 & -0.2 & -0.2 \\ -0.2 & -0.2 & -0.2 & 0.8 & -0.2 \\ -0.2 & -0.2 & -0.2 & -0.2 & 0.8 \end{bmatrix}$$

FIG. 6C

Local average reference
[5×5]

$$\begin{bmatrix} 0.67 & -0.33 & -0.33 & 0 & 0 \\ -0.33 & 0.67 & -0.33 & 0 & 0 \\ -0.33 & -0.33 & 0.67 & 0 & 0 \\ 0 & 0 & 0 & 0.5 & -0.5 \\ 0 & 0 & 0 & -0.5 & 0.5 \end{bmatrix}$$

FIG. 6D

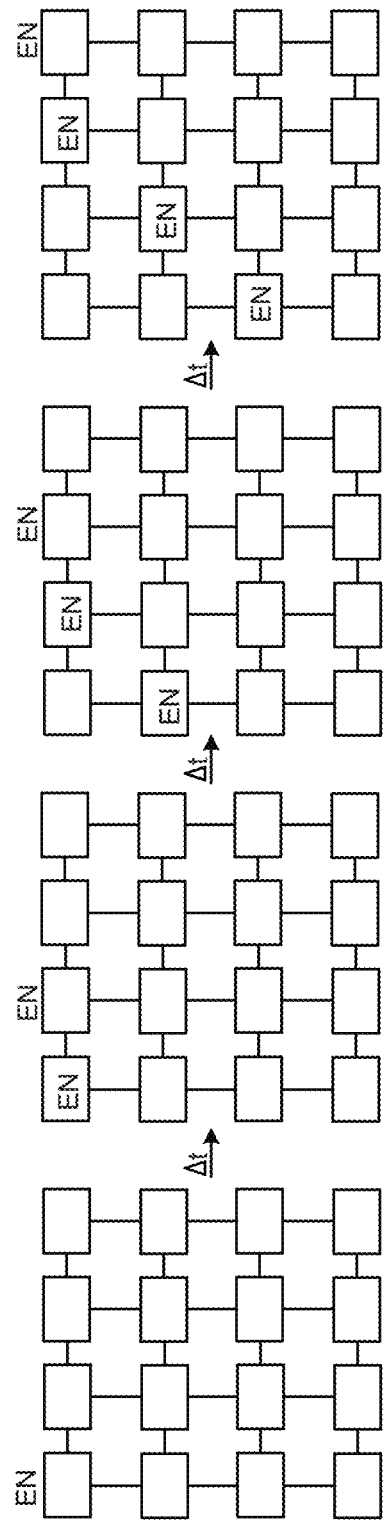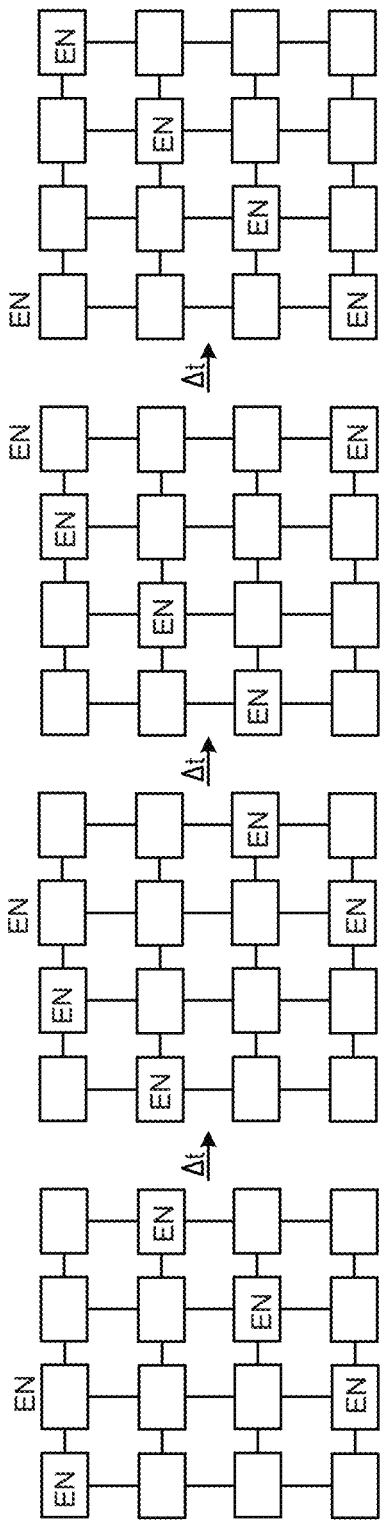

SYSTEMS AND METHODS TO REDUCE DATA AND COMPLEXITY IN NEURAL SIGNAL PROCESSING CHAIN

The present application claims priority under 35 U.S.C. § 119(e) to U.S. Provisional Patent Application No. 62/714,997, filed on Aug. 6, 2018. The contents of the provisional patent application are hereby incorporated by reference in their entirety.

BACKGROUND

Traditional implanted neural devices have performed simple or specific functions in specific regions of neural anatomy, often acquiring data from a limited number of overall sensors (e.g. less than 32 sensors). Because these devices have a clearly defined signal processing chain, customized, static solid-state devices (e.g., application-specific integrated circuits or ASICs) can be designed and optimized to carry out the necessary data processing and analysis. However, as the number of sensors in a neural signal measurement/processing system increases, it has become more challenging to timely process and store the data measured by the sensors. A system with one hundred or more sensors (e.g., two hundred or more, three hundred or more) may need to contend with a similarly increasing amount of data that may be acquired at rates that exceed the processing bandwidth of a controller (e.g., implanted and/or external processor). The system processor or controller must be able to handle large volumes of data in a high-throughput fashion in order to collect as much data as possible to facilitate the thorough characterization of a neural system in nearly real-time. For neural signal measurement/processing systems that are implanted in a patient, and especially systems that are also capable of closed-loop brain stimulation based on the measured signals, a system processor or controller of this level of complexity may present a significant power, area, and throughput challenge. Depending on sensor type, geometry, location (e.g., brain region), and neural data features of interest, measurements from particular sensors may contain redundant or statistically correlated information, and/or may not contain any pertinent data at all.

Accordingly, it is desirable for neural signal measurement/processing system controllers or processors to be able to identify and process neural signals of interest, without diverting computational resources to processing signals from faulty sensors and/or sensors implanted in a patient that are measuring neural activity from a low-activity (or inactive) brain region.

SUMMARY

Described herein are systems and methods for reducing the complexity and size of data payloads delivered to downstream processing from a raw series of neural signal measurements. In one variation, the system may comprise a low-power hardware architecture that combines serially sampled neural signal data with a transformation matrix (TFM) using a novel systolic random-logic-macro (RLM) array. A TFM may comprise weights or matrix values that may select and/or combine and/or suppress signal data from the sensors (e.g., neural activity sensors, sensing electrodes, sensors embedded as part of an implantable electrode) to generate an output data set or data channel vector. In some variations, the output data set or data channel vector may be a reduced data set or data channel vector. A reduced data channel vector may represent a combination of neural signals that contain redundant information, and/or a selection of neural signal data pertaining to a selected neural activity characteristic. In one variation, linearly combining the TFM with the neural activity data acquired from the sensors may comprise a matrix multiplication between the TFM and a data channel vector comprising neural signal data from the sensors. The multiplication may be executed using an array of individually addressable logic blocks, such as RLMs, in a systolic fashion, where the multiplication may be completed in stages across the array. The dimensions of the RLM may be reprogrammable/updateable according to any or all changes to the TFM, and/or changes to the number of sensors and/or quality of the neural signal data acquired by the sensors. In some variations, the TFM may be updated or tuned over time to account for changes in neural activity and/or system parameters, and the RLM array may be dynamically adjusted according to the updated TFM. For example, the RLM array may be resized to smaller or larger array dimensions corresponding to the dimensions of the TFM, and the resizing may be attained through power and clock gating techniques. This may help to reduce the power consumption of the TFM multiplication function, especially when the dimensions of the TFM are reduced over time. In one variation, systolic matric multiplication may comprise serially activating and deactivating RLM elements at each stage of the multiplication. The activation and deactivation of a RLM element may be controlled by an enable signal generated by the system controller (e.g., processor). The activation of RLM elements for particular stages of the matrix multiplication computation (i.e., deactivation of RLM elements when not in use) may facilitate the reduction of energy consumption of the neural sensing and/or neural stimulation system.

The systems and methods described herein may be configured to carry out a linear transformation of neural signal data acquired by sensors of an implanted neural device, and also applicable to sensors of a non-implanted neural device where the sensors are configured to be placed at/or near the scalp of a user, before that data is transmitted to another controller or processor (that may be part of the system components of the implanted device, or may be part of an external device). Neural signal data may not be limited to action potential data (e.g., spike detection, spike counting, spike compression), but may include any local field potentials, including graded potentials, ion channel activity, gap junction activity, and/or any synaptic activity that may result in electric field and/or electric potential changes. In some variations, the systems described herein may also comprise sensors that acquire other physiological signal data that may optionally be used in conjunction with neural signal data to characterize the neural and/or physiological condition of a patient. Examples of physiological signal data may comprise one or more of scalp EEG data, accelerometer data, temperature data, blood pressure data, blood flow data, heart rate data, skin conductance data, patient location data and the like. The methods of linear transformation described in the context of processing neural signal data may also be used to process physiological signal data or any data acquired by the system sensors. Transforming neural signal data using a TFM may help to compress or reduce the data size, which may facilitate the rapid and timely transfer of data between the implantable or non-implantable neural device and an external device. Linear transformation of the neural signal data acquired by the neural device may help to reduce and/or simplify downstream processing steps (e.g. linear transformation can include source/feature separation), and/or may also help improve neural signal data quality. In some variations, linear transformation of the neural signal data using a TFM may remove signal artifacts, such as line noise, redundancies, cross-talk between sensors, and the like. One example of a linear transformation that may be used with any of the systems and methods described herein may comprise re-referencing voltage-based signals. Voltage-based signals represent measurements of the (electric) potential difference between two points (e.g., two locations in a patient body, two locations in a brain region, two locations in a tissue region, etc.). In this example, a data channel vector of voltages may be measured as the difference in electric potential between each vector element's associated electrode and a common (e.g., reference) electrode. Re-referencing may comprise redefining the values of each vector element to an electric potential difference between its associated electrode and a different point, or combination of points. This re-referencing may be accomplished by setting appropriate weights on the TFM before multiplying it with the input signals. Optionally, some variations of the systems and methods disclosed herein may be configured to generate metadata associated with each set of neural signal data and may track and/or update the metadata as the neural signal data is transmitted between system processors and/or between the implantable device and external device. The linear transformation of neural signal data using a TFM may be executed by a processor in the implantable device. In some variations, the linear transformation of neural signal data may be executed by an array of RLMs (in the implantable neural device or non-implantable neural device) that may be dynamically sized according to the TFM. Optionally, the array of RLMs may be configured for systolic matrix multiplication of the TFM and a neural data vector (e.g., a data channel vector), in combination with sequential channel sampling, which may help facilitate the rapid processing of data acquired by a high-signal-count implantable device.

One variation of a method for detecting neural activity may comprise acquiring neural signal data from a plurality of M sensors to generate a data channel vector having M data channels, generating a transformation matrix (TFM) comprising an M×N matrix of matrix values, configuring an array of individually addressable logic blocks to have M×N active logic blocks, where each logic block comprises a memory element that stores a matrix value of the TFM corresponding to each logic block, and generating an output data channel vector having N data elements by multiplying the data channel vector with the TFM using the M×N array of logic blocks. The matrix values of the TFM may be determined by identifying data channels with high-noise neural signal data and assigning a zero value to the matrix values in rows of the TFM that correspond to the identified high-noise data channels, identifying data channels in the data channel vector with correlated neural signal data, and iterating through matrix values to compute non-zero matrix values for rows of the TFM that correspond to the identified correlated data channels, wherein the non-zero matrix values combine neural signal data of the correlated data channels. The method may optionally comprise displaying the matrix values of the TFM on a monitor. In some variations, the logic block array may be located in an implantable device and the method may further comprise transmitting the output data channel vector from the implantable device to an external controller. The plurality of M sensors may be configured to be attached to the implantable device and/or may be implantable into or in contact with brain tissue, and the data channel vector may be configured to be transmitted from the implantable device to a processor of the external controller. In some variations, the TFM may be generated using the processor of the external controller and transmitted to the implantable device. Configuring the logic block array may comprise providing a gating enable signal to the M×N active logic blocks. Alternatively or additionally, configuring the logic block array may comprise providing a gating enable signal to a number of active logic blocks that correspond with the number of non-zero matrix values of the TFM, and/or providing a gating power signal to the M×N active logic blocks. In some variations, identifying data channels with correlated neural signal data may comprise calculating a correlation coefficient between pairs of data channels and clustering data channels according to the calculated correlation coefficients. Identifying data channels with neural signal data with high levels of noise may comprise comparing a magnitude of predetermined spectral components of neural signal data of the M data channels and identifying the data channels that have a magnitude of predetermined spectral components greater than a predetermined threshold value. Generating the TFM may comprise assigning a zero value to the matrix values that correspond with the data channels with high levels of noise. Generating the TFM may further comprise identifying valid data channels with neural signal data that have noise levels below a noise threshold, and assigning a non-zero value to the matrix values that correspond with the valid data channels.

In some variations, generating the TFM may further comprise iterating through matrix values such that multiplying the data channel vector with the TFM selects the data channels that have neural signal data pertaining a neural activity characteristic. For example, the neural activity characteristic may comprise a frequency component of the neural signal data, where the frequency component comprises neural signal data in the beta frequency band (15-30 Hz). Some variations may comprise generating a data validity flag for each data channel of the data channel vector indicating whether a data channel contains neural signal data having noise levels that exceed a noise threshold. Each logic block of the logic block array may comprise a multiplication circuit and an addition circuit. The logic block array may be configured as a systolic matrix multiplier. In some variations, the M sensors may comprise M electrodes connected to an analog-to-digital converter (ADC), and the method may further comprise generating the TFM if an impedance of an electrode exceeds a pre-determined threshold or if neural signal data measured by the electrodes is outside of an operating range of the ADC. In some variations, the method may comprises generating the TFM when the neural signal data is clipped by the ADC. The TFM may be a bipolar-type matrix, a Laplacian-type matrix, a global weighted average matrix, or a local weighted average matrix. Generating the TFM may occur during a calibration session after the sensors have been implanted in or on brain tissue. The sensors may be implanted into brain tissue, and generating the TFM may occur when one or more of the plurality of implanted sensors has shifted position within the brain tissue, and/or when trauma to the brain tissue has been detected. In some variations, a first sensor may have been implanted into or in contact with a first functional brain region and a second sensor may have been implanted into or in contact with a second functional brain region that is different from the first functional brain region. Some variations may comprise transmitting the output data channel vector to an external controller and reconstructing an approximation of the data channel vector using the external controller by multiplying the output data channel vector with an inverse of the TFM. Optionally, N<M and the output data channel vector may be a reduced data channel vector.

One variation of a method for acquiring and processing neural signal data acquired by a measurement system may comprise acquiring neural signal data from a plurality M of sensors in contact with neural tissue, where the neural signal data forms a data channel vector having M channel elements, multiplying the data channel vector with a M×N transformation matrix (TFM) of data channel values to remove neural signal data redundancies and noise artifacts, where the product is a reduced data vector having N data elements, wherein N<=M, and transmitting the reduced data vector to an external controller. The method may further comprise generating a data validity flag for each data channel of the data channel vector indicating whether a data channel contains neural signal data having noise levels that exceed a noise threshold. A data validity flag may be generated if the neural signal data corresponds to a malfunctioning activity sensor and/or has signal noise levels that exceed a predetermined noise threshold. Multiplying the data channel vector with the TFM may comprise performing systolic matrix multiplication using a logic block array located inside an implanted measurement system controller. The logic block array may comprise one logic block per non-zero data channel value of the TFM and each logic block comprises a memory element that stores a non-zero data channel value of the TFM. Performing systolic matrix multiplication may comprise sequentially activating logic blocks to sequentially multiply data channel values of the TFM with the channel elements of the data channel vector, and sequentially deactivating logic blocks in synchrony with a system clock signal. Sequentially activating logic blocks and deactivating logic blocks may comprise providing an enable signal to each logic block, where a high value on the enable signal to a logic block may activate the logic block and a low value on the enable signal to a logic block may deactivate the logic block.

BRIEF DESCRIPTION OF THE DRAWINGS

FIG. 5A depicts a pseudocode representation of one variation of a method for generating a metadata flag or indicator that may be linked with neural signal data contained in a data channel at a particular time point.

FIGS. 5B-5C depict examples of how a metadata flag that indicates the validity of neural signal data in a data channel may be propagated during processing of that neural signal data.

FIGS. 6A-6D depicts various examples of a transformation matrix.

FIGS. 9A-9H depicts one example of the propagation of an enable signal EN across a logic block array in systolic matrix multiplication.

DETAILED DESCRIPTION

Figure 1:
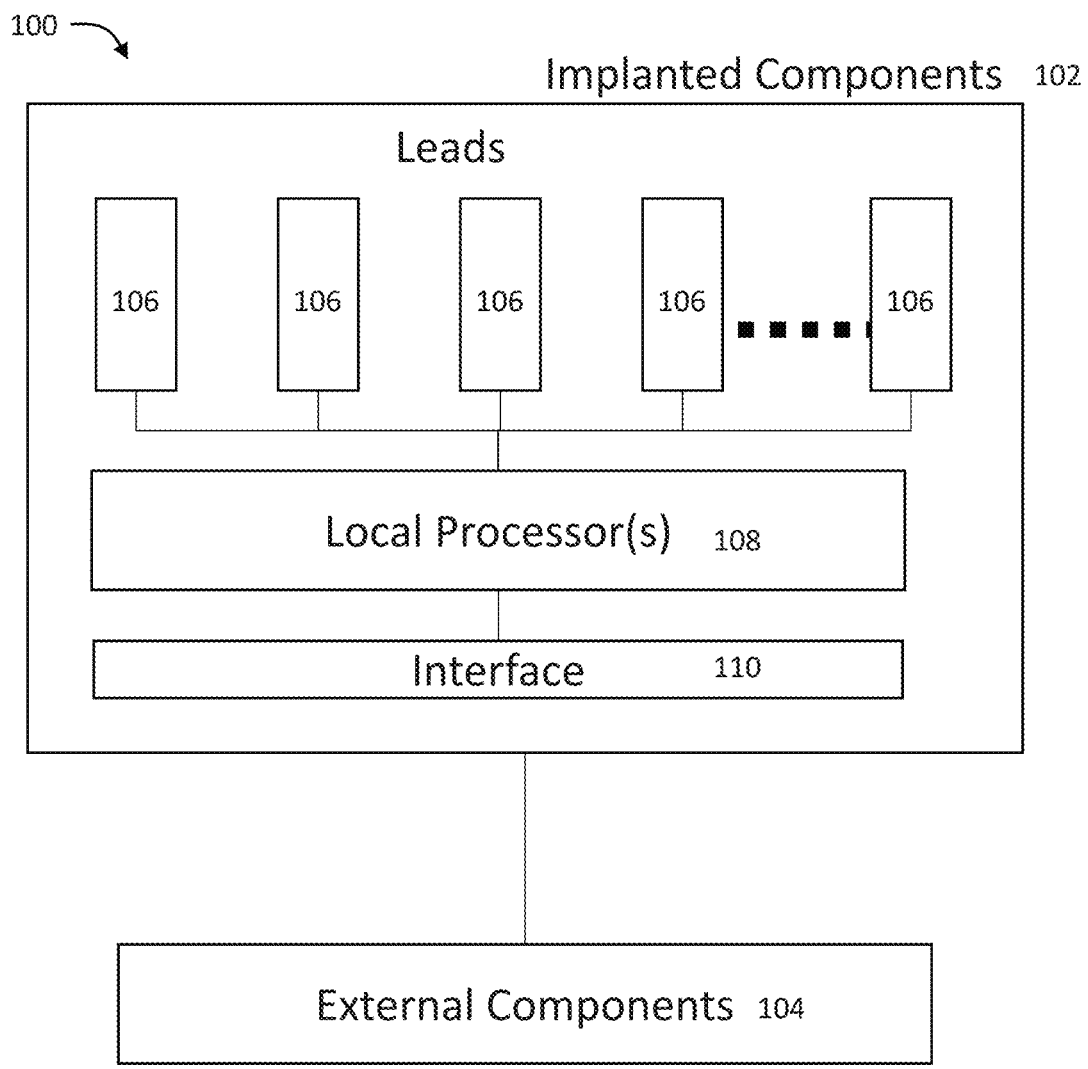
FIG. 1 depicts a schematic representation of a system for measuring neural activity data and/or signals.

Described herein are systems and methods for reducing the complexity and size of data payloads delivered to downstream processing from a raw series of neural signal measurements. In one variation, the system may use a low-power hardware architecture that linearly combines serially sampled neural signal data with a transformation matrix (TFM) using a novel systolic random-logic-macro (RLM) array. A TFM may comprise weights or matrix values that may select and/or combine and/or suppress neural signal data from the neural signal sensors (e.g., implantable or non-implantable sensors embedded as part of sensing electrodes) to generate a reduced data set or data channel vector. The reduced data channel vector may represent a combination of neural signal data that contain redundant information, and/or a selection of neural signal data pertaining to a relevant neural activity characteristic. The data reduction methods described herein account for the characteristics of acquired signals when calculating the TFM so that irrelevant or unwanted signal components (i.e., information contained in the signals which is not sufficiently useful to the system) are suppressed or removed, and relevant signal components (i.e., information contained in the signals which is sufficiently useful to the system) is processed, recorded, and/or transmitted. By selectively removing certain signal components while retaining others based on the neural signals acquired by a high-sensor count neural implant using a linear transformation, the reduced set of neural signal data may contain information that includes combinations of channels with correlated or redundant data, along with separate channels with unique data. For example, the reduced neural signal data set may contain information such as mixed correlation and independence between signals recorded on different sensors or channels, and mixed amounts of correlation in recorded noise across channels.

Implantable or non-implantable neural systems that include the linear transformation features described herein may be configured to compress or reduce the data payload so that the number of sensors can be increased or further scaled up, allowing for the acquisition of additional neural signal data (e.g., greater sampling over a brain region, greater sampling over a broader region of tissue, and/or additional types of neural signals), while still operating within bandwidth limitations of a data transmission interface between the implantable portion of a system and an external processor. In one data acquisition use-case, neural systems with a large number of sensors may generate large data payloads, which may potentially prevent complete raw data frames from being transmitted to an external device due to bandwidth limitations. Reconfigurable data processing capabilities may facilitate the extraction and transmission of the neural signal information of interest, which may help such data to be acquired and stored without exceeding bandwidth capabilities or power limitations of, for example, the implantable portion of the system. Dynamically updating the linear transformation parameters may allow the system to adapt to changing neural conditions and/or sensor conditions (e.g., temporary or permanent disabling of certain sensors, sensors reaching end-of-life, dislodged and/or faulty sensors, changing implantation conditions, etc.).

As described above, a neural signal measurement, processing, and/or recording system with a large number of measurement sensors may acquire more data than can be transferred over its communication interface. Processing such large quantities of data using, for example, an implanted controller processor may be challenging, since implanted processors are often constrained by size and power consumption (e.g., battery capacity). The neural signal data reduction methods described herein may utilize certain characteristics of the acquired neural signal data in order to reduce the quantity of data for transmission and/or processing. For example, recording system having large numbers of sensors may contain groups of one or more data channels with neural signal data that are independent from the neural signal data contained in one or more other data channels or groups of channels. These various sets of mostly-independent neural signal information may be kept separate from each other using a TFM having, among other properties, a large proportion of zero valued matrix elements. In systems with large numbers of recording sensors, there may be one or more sensors or data channels that contain unusable or invalid data. For example, the impedance of some electrodes may exceed an acceptable threshold. When a sensor or data channel is determined to be containing invalid data (e.g., due to a faulty sensor or temporary signal disruption), a metadata field associated with a data channel vector containing neural signal data acquired at that time may be set to a value indicating that the data is invalid. For example, the metadata field may be a sample-valid field, where a value of "1" indicates the data is valid and a value of "0" indicates the data is invalid. In some variations (e.g., where the TFM is sparse), this metadata field information may be propagated to downstream processors to identify which data channel vectors have reliable and/or usable neural signal data. Sparse TFMs, where many of the matrix values are zero, may be used to separate and/or maintain the independence of data channels that contain neural signal data pertaining to any desired (e.g., different) neural characteristics. Where groups of data channels are largely independent, the system may carry out a sparse reduction and propagate metadata indicating the validity of neural signal data for certain data channels. This may facilitate, for example, the retention of useful data in one group even if data is invalid in the other.

Systems

FIG. 1 is a schematic depiction of one variation of a system for measuring neural signal data. A neural signal measurement/processing system may be included with, e.g., a therapeutic system (e.g., with programming stimulation circuitry), a diagnostic system, or a research system. A neural signal measurement/processing system (100) (or simply "system (100)") may comprise implantable components (102) and external components (104) that are not implanted in a patient body.

The external components (104) may comprise one or more of a display, controller and/or processor, user interface elements (e.g., buttons, indicia, joystick, keyboard, touch screen, etc.), and may comprise a communication interface for transmitting and receiving signals to and from the implantable component (102). In some variations, external components (104) may be implemented by a handheld tablet, smartphone, and/or any other suitable computing device. The communication between the implantable component and the external component may be wireless and/or wired.

The implantable components (102) may include one or more leads or sensors (106) that are configured to be placed at various brain or skull regions, an onboard processor (108), and a communication interface (110) for transmitting and receiving signals to and from the external components (104). In some examples, the implantable components (102) include an implantable device configured to house and/or be connected to one or more of the other implantable components (102). The implantable device may be configured to be implanted within a head of a patient and/or at any other suitable location with a patient as may serve a particular implementation.

A lead (106) may comprise one or more sensors configured to detect neural signal data. For example, the one or more sensors may be one or more electrodes that may be distributed along the surface and/or length of the lead, and connected to one or more corresponding wires within the lead. Some or all of the electrodes may be separate or independent from each other such that electrical signals on the electrodes are kept separate (e.g., not electrically connected to each other), while some or all of the electrodes may be connected together so that electrical signals are shared (e.g., electrically connected to each other via and internal wire in the lead). Each lead (106) may have any number of sensors, for example, 1, 2, 3, 4, 6, 8, 10, 12, 24, 32, 36, 48, 50, 64, 96, 100, 128, 140, 200, 256, or more sensors. Alternatively or additionally, one or more leads may comprise non-electrophysiological sensors, for example, accelerometers, temperature sensors, pH sensors, heart rate, and/or blood flow sensors, etc. that acquire non-electrophysiological signals.

The one or more sensors disposed on lead (106) may, in some examples, be attached (e.g., communicatively coupled) to an implantable device that implements system (100) and may be configured to be implantable into or in contact with brain tissue. This may be performed in any suitable manner. For example, a first sensor may be implanted into or in contact with a first functional brain region and a second sensor may be implanted into or in contact with a second functional brain region that is different from the first functional brain region.

The neural signal data collected on the leads (106) may be transferred via internal wires to a local processor (108) in the implantable device. In one variation, the neural signal data from each of the sensors may be used by the local processor to form a data channel vector, where the number of vector elements corresponds to the number of individual sensors; that is, for a system with M individual sensors, the local processor may form a data channel vector with M vector elements. Each vector element may correspond to neural signal data acquired on a particular sensor at a particular point in time, and the data channel vector represents all of the neural signal data acquired over all M sensors at that particular point in time. Alternatively or additionally, each vector element may correspond to neural signal data acquired by a single sensor or by multiple sensors at sequential points in time. For example, an M-length data channel vector may comprise neural signal data acquired by a sensor over M sequential points in time, or an M-length data channel vector may comprise neural signal data acquired from a plurality of sensors over M sequential points in time. The local processor (108) may comprise analog recording electronics and digital signal processing circuitry that are configured to record and/or modify the neural signal data in the data channel vector for downstream data transfer and/or processing. For example, the local processor may comprise an array of individually addressable logic blocks (which may each include, for example, a multiplication circuit and an additional circuit), such as random-logic macros or RLMs, that may be configured to suppress and/or remove noise, neural signal information that is not relevant to a neural characteristic of interest, consolidate or otherwise aggregate neural signal data that may be redundant or correlated, and/or amplify or boost neural signal information pertaining to a neural characteristic of interest. In some variations, the local processor (108) may comprise a general purpose processor, Field Programmable Gate Array (FPGA), an Application Specific Integrated Circuit (ASIC), or the like. The processor (108) may be configured to run and/or execute application processes and/or other modules, processes and/or functions associated with the system and/or a network associated therewith (not shown), and may comprise one or more memory elements. The communication interface (110) may be configured to transmit and receive signals from the external components (104) via a wired connection and/or a wireless connection (e.g., via Wi-Fi, Bluetooth, etc.). The data transfer bandwidth between the implantable components and the external components may have an upper data payload throughput limit. As the number of leads and/or sensors on the leads increases, the processor (108) may be configured to reduce or compress the neural signal data (e.g., using any of the transformations described herein) in the data channel vector so that the data volume that is to be transferred to the external components does not exceed the data throughput limit of the communication interface (110). For example, one variation of a system for measuring neural activity data may comprise an array of 96 sensors (e.g., electrodes), and the local processor may form a data channel vector with 96 elements. The local processor may be configured to reduce the data channel vector from having 96 elements to having 32 elements, which may be within the bandwidth limit of the communication interface. Optionally, the implantable components (102) may comprise stimulation circuitry and/or leads.

One variation of a local processor may comprise an array of individually addressable logic blocks or RLMS where the individual blocks or RLMs are sequentially enabled/activated and disabled/deactivated in a pipelined fashion, where the logic blocks that are involved in the immediate computation are enabled and the other logic blocks are disabled. For example, the array of logic blocks or RLMs may be configured for systolic data processing. The enabling and disabling of logic blocks may be controlled by one or more enable signals and/or power signals provided in synchrony with a processor clock signal. Neural signal data may be serially sampled by the processor, which may then process each data sample sequentially in a pipelined fashion. Such sequential activation and deactivation of logic blocks may help reduce dynamic power consumption of the local processor by only enabling and/or powering a small subset of the logic block array at any one time. The computations involved in the linear transformation of channel data may be carried out by a number of different protocols, calculating independently for each time point the signal transforms across all channels, and/or pipelining steps of the calculation so that multiple time points are being processed at different stages within the pipeline. The calculation may also be performed for a range of time points after accumulating the channel data within a larger frame of time points. In the case of a systolic matrix multiplication, the data values for successive data channels of an input vector may be delivered sequentially to the multiplication and summation hardware.

The neural activity measurement systems described herein may be used for research, diagnostic and/or therapeutic applications. In one variation, a neural signal measurement/processing system may be implanted into a patient. After implantation, a clinician may power on the implanted portion of the system (e.g., the implanted device) and may begin a training/calibration procedure in which raw neural signal data from the implanted device is streamed into an external machine with greater processing capabilities. The external controller may have a processor configured to aggregate neural signal data over a specified, prolonged, time course (e.g., seconds of data), and may use the acquired neural signal data to generate a transformation matrix (TFM) that may be used to reduce or compress neural signal data to contain information of interest. Decompression to reconstruct recorded signal information (possibly with loss) may comprise multiplication of the inverse (or pseudoinverse) of the TFM matrix with the reduced signals. Another example would be to construct the transformation matrix in a way that produces a number of signals which are each composed mostly of information in a limited frequency band.

In some variations, the external controller processor may use statistical and/or machine learning algorithms to calculate matrix values for the TFM. The determination of the matrix values may be computed using an iterative process and/or predetermined algorithms to identify matrix values that satisfy signal quality and size constraints. Some examples of signal quality constraints may include the degree of correlation between each signal and other externally-measured signal(s)-of-interest, the degree of correlation between each signal and other externally measured noise signal(s), the signal amplitude in frequency bands which have been previously determined to contain information useful to device performance, the signal amplitude in frequency bands which have been previously determined to not contain information useful to device performance, shared information between signals, etc. The TFM may be transmitted to the implanted device where the matrix values may be stored in a programmable memory of the processor of the implanted device. The TFM may be re-calculated as may be desired, for example, in retraining or recalibration sessions. The matrix values of the TFM may be tuned or adjusted over time, and the adjusted matrix values may be transmitted to the implanted device and stored in processor memory. In some variations, the TFM may be linearly combined with a data channel vector containing neural signal data acquired by the sensors to generate an output data channel vector (e.g., a reduced data channel vector) that may be transferred over the communication interface without exceeding the data bandwidth limits of the interface. In cases where the logic block array is located in an implantable device that implements implanted components (102), the implantable device (i.e., a component included within the implantable device) may transmit the output data channel vector to an external controller. This is described in more detail herein.

In some examples, local processor (108) is configured to configure the logic block array. For example, local processor (108) may configure the logic block array by providing a gating enable signal to the M×N active logic blocks. Additionally or alternatively, local processor (108) may configure the logic block array by providing a gating enable signal to a number of active logic blocks that correspond with the number of non-zero matrix values of the TFM. Additionally or alternatively, local processor (108) may configure the logic block array by providing a gating power signal to the M×N active logic block.

Linear Combination of Neural Signal Data with a Transformation Matrix

Figure 2A:
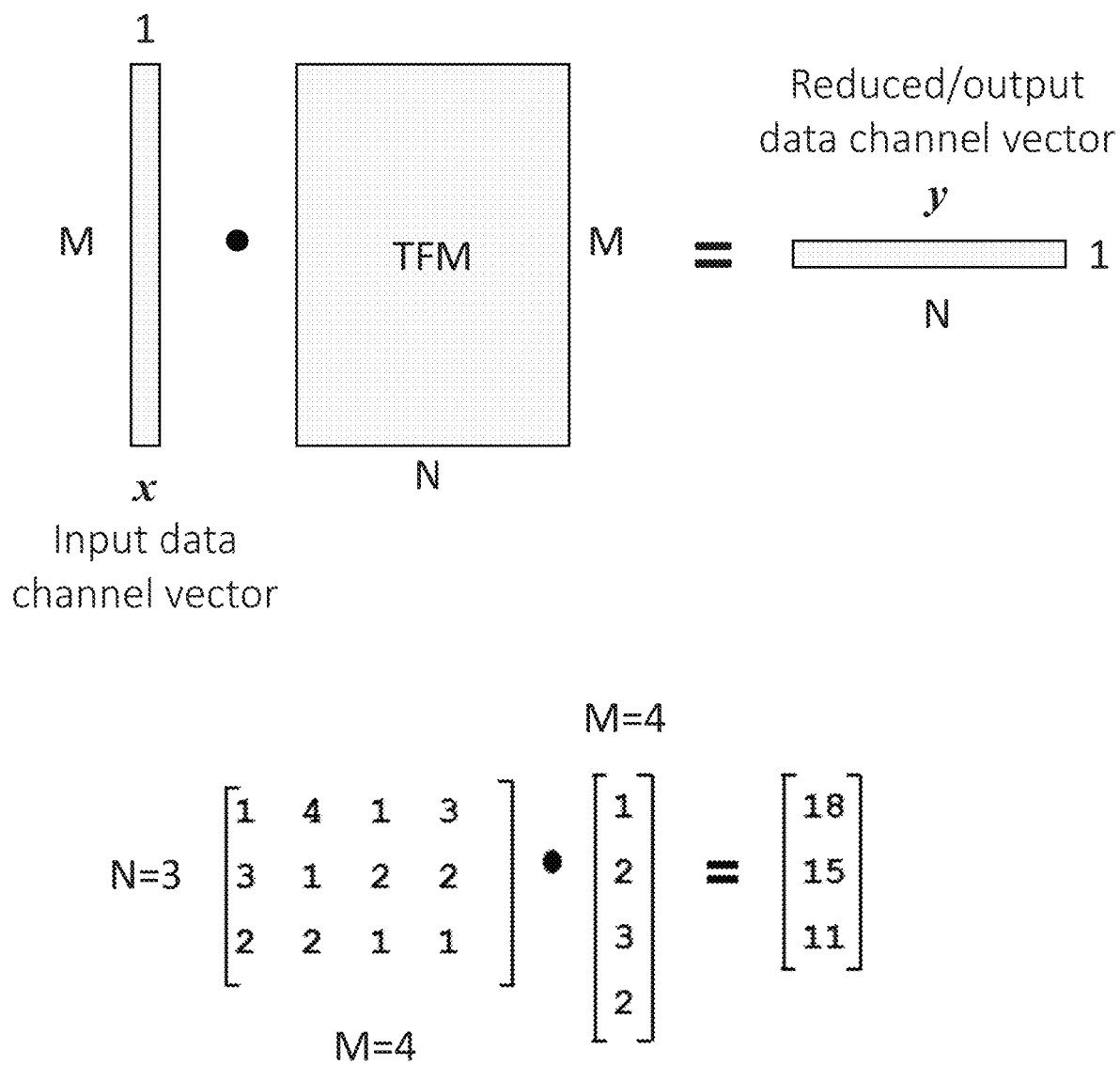
FIG. 2A depicts a graphical representation and an example of modifying an input data channel vector with a transformation matrix.

FIG. 2A is a conceptual depiction of how a linear combination of recorded neural signal data with a transformation matrix (TFM) may be used to reduce neural data throughput for transmission and/or downstream processing. FIG. 2A depicts a multiplication of a data channel vector x having M elements (i.e., an M×1 matrix) with a TFM that has M rows and N columns, where each element $x_i$ of the data channel vector is neural signal data recorded within a small time Δt of a sample time $t_i$ from M sensors. In some examples, N is less than M. In other examples, N is less than or equal to M. The data channel vector x may comprise data channels $x_1$ to $x_M$. The product of multiplying data channel vector x with the TFM may be an output data channel vector y:

$$y = TFM \cdot x(t_s),$$

where $t_s$ is the time at the end of the interval of all the most recent sample times $t_i$ for the M channels. In the case where N<M, data channel vector y may have fewer elements than the data channel vector x; accordingly, the output data channel vector y may be referred to as a reduced data channel vector. The lower portion of FIG. 2A provides a numerical example, with M=4 and N=3. This linear operation may convert a larger-dimension data channel vector into a smaller-dimension data vector (i.e., a reduced data channel vector). Each of the N data channels in the output data channel vector (which corresponds to a column in the TFM) may be a sum of the products of each data channel in the original (larger-dimension) data channel vector with the corresponding matrix values in that column of the TFM. The matrix value of the TFM in the corresponding row may determine the contribution of each data channel in the original data channel vector in the sum. A zero matrix value in a row position corresponding to a particular data channel may eliminate the contribution of that data channel to the sum. A non-zero matrix value in a row position corresponding to a particular data channel may include the contribution of that data channel to the sum, but the value of the matrix value in that row relative to the other non-zero matrix values in that column may determine the relative contribution of that particular data channel as compared to other data channels. For example, in such manner, the matrix values of a TFM may be generated such that data channels containing neural signal data of interest contributes to the elements in the output data channel vector (e.g., by multiplication with a non-zero matrix value and summed over all the rows), while data channels with irrelevant or faulty signal data may be eliminated (e.g., by multiplying with a zero matrix value). The channel sample times $t_i$ may not be be identical, although they may all fall within an interval $t_{(s-1)} < t_i <= t_s$. That is, neural signal data included in a data channel vector may be recorded from different sensors that may be sampled at different sampling rates.

Figure 2C:
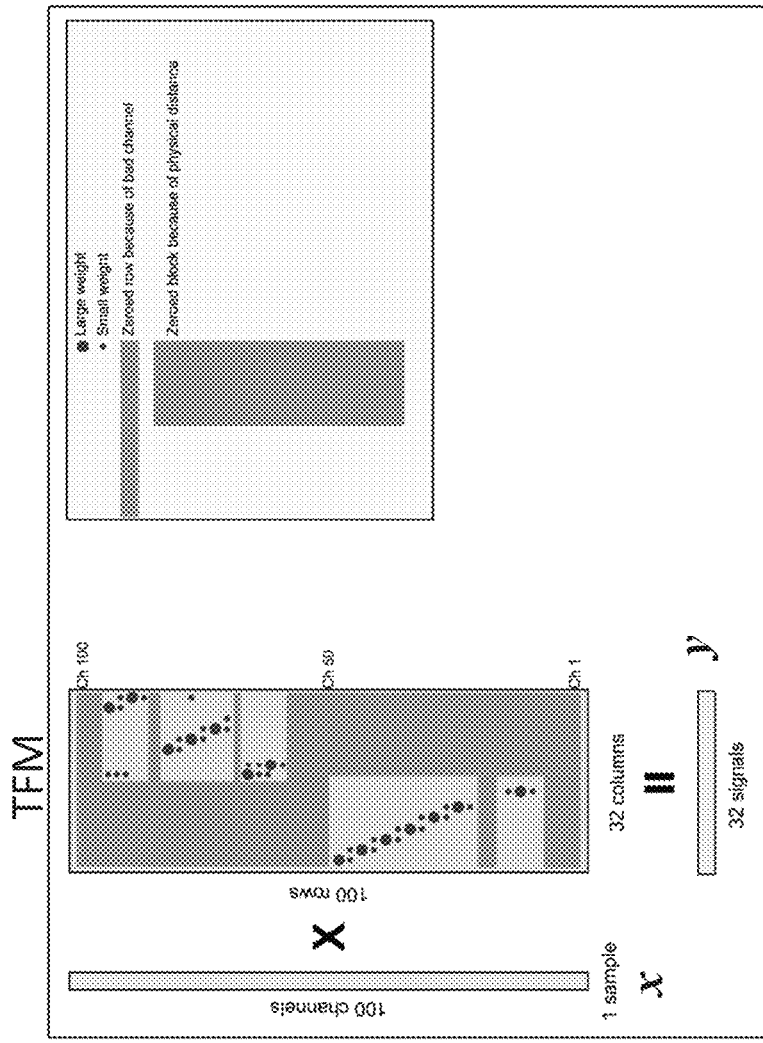
FIG. 2C depicts a graphical representation of modifying an input data channel vector comprising data from the leads of FIG. 2B with a transformation matrix.
Figure 2B:
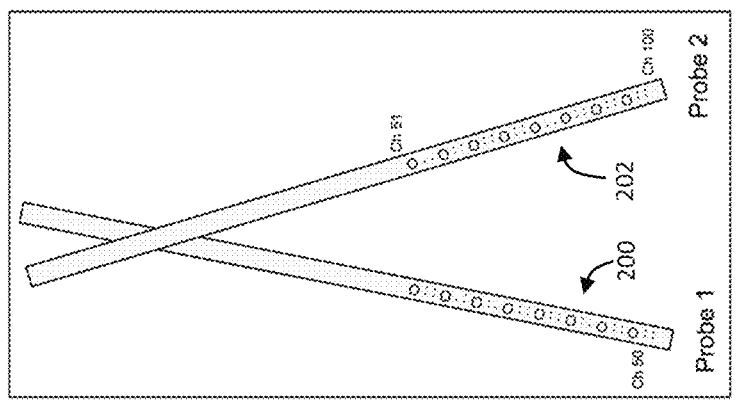
FIG. 2B depicts one variation of a system of measuring neural activity data comprising two leads or probes.

FIG. 2B depicts an example of a system of measuring neural activity data comprising two leads or probes (200, 202), where each lead has 50 sensing electrodes corresponding to 50 data channels. The first lead (200) may have data channels 1 to 50 and the second lead may have data channels 51 to 100. FIG. 2C depicts a data channel vector x with 100 data channels (M=100), where data channels 1-50 contain neural signal data collected by electrodes 1-50 on the first lead (200) and data channels 51-100 contain neural signal data collected by electrodes 51-100 on the second lead (202). In this example, the reduced data channel vector y has 32 elements (N=32), and the TFM is therefore a 100×32 matrix, where each row corresponds to a data channel of the data channel vector x (i.e., in a corresponding row of vector x) and each column corresponds to a data channel of the reduced data channel vector y (i.e., in a corresponding column of vector y). The TFM may be used to reduce 100 input channels to 32 signals. In this example, data channels 1-16 of the vector y may include neural signal data from channels 1-50 and data channels 17-32 of the vector y may include neural signal data from channels 51-100. Since channels 1-50 and 51-100 are on different probes and in this example, may be implanted in two distant (e.g. anatomically and functionally distinct, non-overlapping) brain regions, the rows of the TFM corresponding to data channels 51-100 of vector x in the columns of the TFM corresponding to data channels 1-16 of vector y may have matrix values of zero, while the rows of the TFM corresponding to data channels 1-50 of vector x in the columns of the TFM corresponding to data channels 17-32 of vector y may have matrix values of zero (see FIG. 2C). In this example, data channels 95-100 may be zeroed out by assigning matrix values of zero for the corresponding rows in the TFM. These channels may be eliminated from downstream analysis and processing for a variety of reasons, including, but not limited to, those sensors being faulty/damaged, and/or implanted at regions that are not of interest, and/or having high noise levels. Large and small matrix values are represented as large and small circles, respectively, in the TFM. Empty areas in the TFM denote zero weights imposed by a sparsifying matrix value generation method, while empty rows denote zero matrix values set either to exclude "faulty" channels and/or to reflect the separation of probe signals by distance. The resulting weight matrix may be very sparse with fewer than 40 non-zero weights out of 3200 possible weights.

Figure 3A:
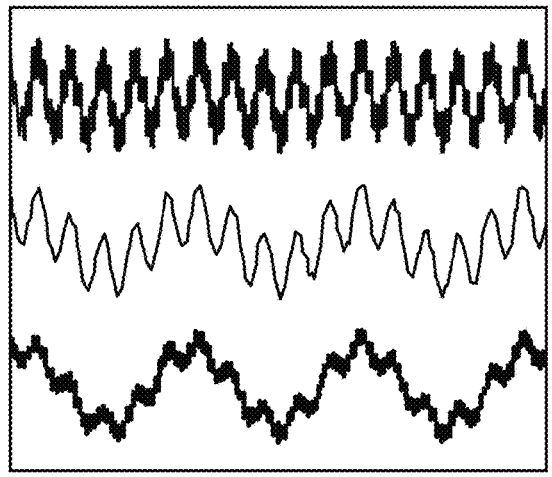
FIGS. 3A-3D depict one example of how a linear transformation with a TFM may be used to reduce the number data channels in a data channel vector by removing or suppressing a data channel that is noisy.
Figure 3B:
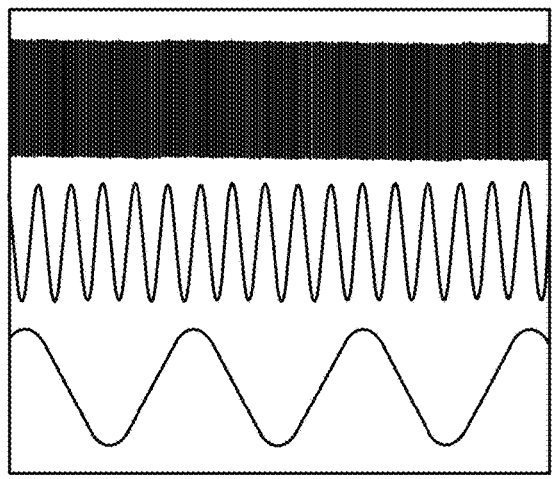
Figure 3C:
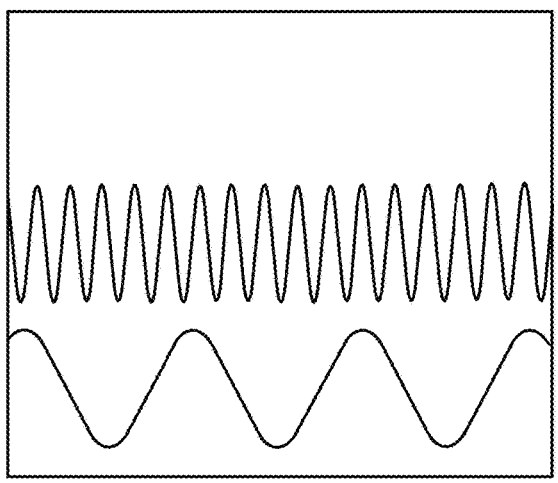
Figure 3D:
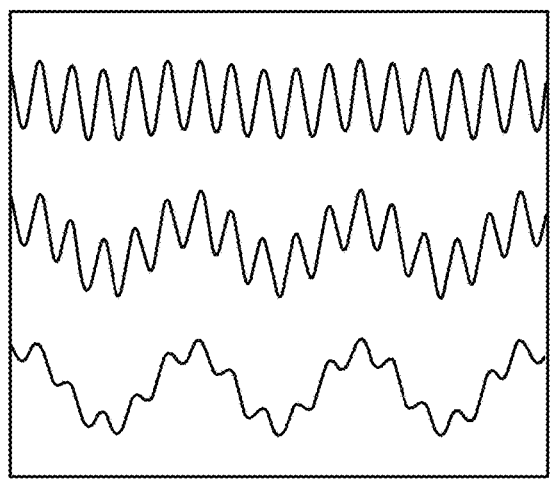

FIGS. 3A-3D and 4A-4C depict examples of linear transformation of neural signal data for reducing data volume and suppression of noise and/or unwanted artifacts, while maintaining the separation of data channels with uncorrelated or unique neural signal data. FIGS. 3A-3D depict one example of how a TFM may be used to reduce the number data channels in a data channel vector by removing or suppressing a data channel that is noisy. Linear transformation of signals acquired by the implant may separate distinct signal sources and features, and may be used to improve the signal-to-noise ratio. FIG. 3A depicts three examples of neural signal data recorded on three channels that contain mixed information from signal sources (e.g. different neurons, line noise). FIG. 3B depicts the signals resulting from applying a linear transformation to the data channel vector with a TFM, which may separate distinct signal sources. In FIG. 3C, the top signal was removed due to matching features consistent with noise (e.g. a high proportion of total power around the 60 Hz frequency band, consistent with line noise) This may be attained by first modifying the TFM by removing the row which corresponds to the noisy signal and then multiplying the signals in FIG. 3A by this modified TFM. In effect, the three signals from FIG. 3B were reduced to 2 signals in FIG. 3C. The top (noisy) signal in FIG. 3B is not stored or transmitted, thereby reducing the data volume for storage and/or transfer. FIG. 3D depicts the lossy reconstruction (decompression) of the remaining signals in FIG. 3C, producing 3 signals that resemble the recorded signals in A, but without the signal contribution that was removed. These signals can be obtained by first computing the inverse (or pseudo-inverse) of the modified TFM with the removed row (TFM$^{-1}$), and then multiplying TFM$^{-1}$ with the signals in FIG. 3C.

Figure 4A:
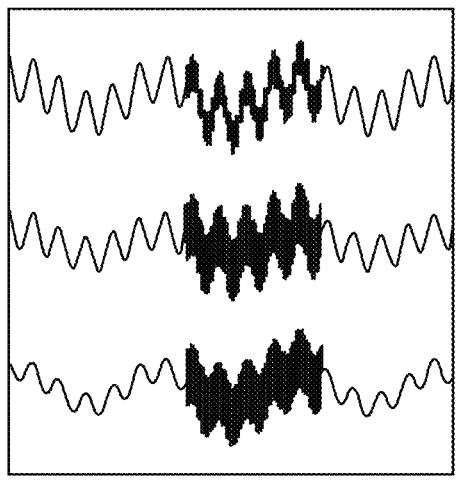
FIGS. 4A-4C depict one example of how a linear transformation with a TFM may be used to remove or suppress a data channel that is noisy.
Figure 4B:
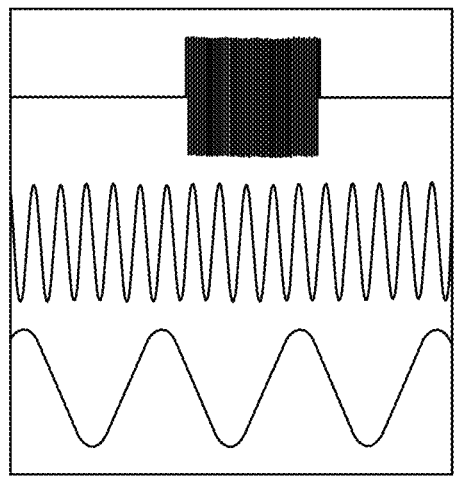
Figure 4C:
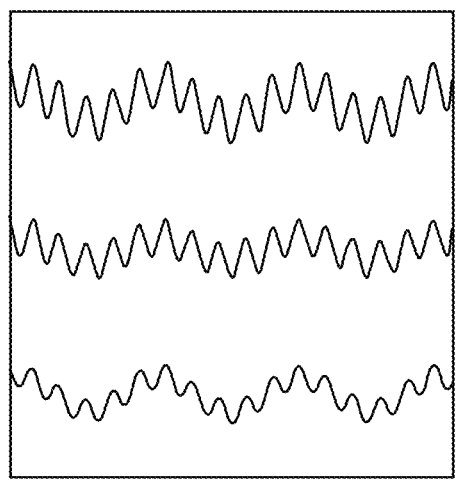

FIGS. 4A-4C depict another example where a linear transformation of the acquired neural signal data may facilitate the removal of unwanted noise or interference artifacts. FIG. 4A depicts three examples of neural signal data recorded on three channels that contain mixed information from signal sources (e.g. different groups of neurons) and a noise artifact that appears on all three channels in the middle third of the time interval shown. A linear transformation with TFM was found which, when applied to the neural signal data of FIG. 4A, separates out each of the signal sources, and FIG. 4B depicts the neural signal data resulting from that linear transformation. As may be seen in FIG. 4B, the top trace corresponds to a signal component containing the noise artifact that is responsible for the increased noise levels in all of the data channels. A second transformation matrix TFM* may be computed (using any of the methods described herein) to remove the noise artifact by matrix multiplying the inverse (or pseudoinverse) of TFM with a modified version of TFM in which the row corresponding to the noise component was set to zero. This second transformation matrix, TFM*, may then be multiplied with the signals in FIG. 4A to obtain the signals in FIG. 4C. FIG. 4C depicts the reconstructed neural signal data of the three data channels. As depicted there, these signals resemble the recorded signals depicted in FIG. 4A, but without the pronounced effect of the noise artifact. Alternatively, the noise artifact may be removed by multiplying input signal with TFM to get an intermediate signal, zeroing out channels in the intermediate signal (e.g., the channels containing the noise artifact) to obtain a modified intermediate signal, and multiplying the modified intermediate signal with the inverse of the TFM to reconstruct the neural signal data of the three data channels.

Metadata Generation and Management

In some variations, the data from a sensor may sometimes contain usable, valid neural signal data, and at other times, contain unusable, invalid data. For example, sensor positions may shift depending on a patient's position or posture, resulting in some sensors containing valid neural signal data at certain times and invalid neural signal data at other times (e.g., sensor(s) becomes dislodged and/or loses contact with brain tissue of interest). Instead of, or in addition to, the TFM rows corresponding to those position-variant sensors being assigned zero matrix values, an indicator or flag may be generated for each data channel at each acquisition or recording time point that indicates the validity of that data sample from that data channel. In some variations, such an indicator or flag may be used in cases where the generated TFM is sparse, i.e., has many matrix values of zero. For example, if many of the sensors of a neural activity measurement system have been damaged (e.g., during implantation and/or over time), and/or are recording noisy and/or otherwise unusable signal data, the generated TFM may have many zero-value matrix values, and therefore, it may not be desirable to disregard or ignore neural signal data on one (or a few) data channels all of the time. However, this may be counterbalanced against assigning a non-zero TFM matrix value for that data channel, and risk invalid data from that channel corrupting all transformed signal rows at a particular acquisition time point. In one variation, whenever the data in a data channel is invalid, such validity status is reflected in a generated indicator or flag associated with the transformed output. The indicator or flag may note whether any of the data channels having a non-zero TFM matrix value (i.e., neural signal data from that data channel may contribute to an element of a transformed data channel vector) contain valid neural signal data. Examples of reasons that would mark an input data channel as having invalid or unusable signal data may include the impedance of the sensor corresponding to that data channel exceeding a threshold or the analog-to-digital converter (ADC) clipping at min/max input values (i.e. the true input value becomes unknown), position and/or movement and/or location detector(s) associated with a lead that indicates a position shift that exceeds a predetermined threshold, and/or the detection of elevated levels of high-frequency spectral components in the neural signal data. This indicator or flag may be associated or linked with each data channel and propagated to downstream processors, so that a decision may be made as to whether the acquired neural signal should be stored or transmitted for further processing, or discarded.

One variation of a method for generating a metadata flag or indicator that may be linked with neural signal data contained in a data channel at a particular time point is represented in pseudocode in FIG. 5A. Each sensor or data channel corresponding to an element of the input data channel vector x (e.g., having M elements) may have its own data validity flag or indicator SAMPLEVALID generated by system (100), while each data channel of the output data channel y (e.g., having N elements) may have its own data validity flag or indicator ELVALID. If the SAMPLEVALID flag of a sensor or data channel of the input data vector x that has a matrix value with a magnitude greater than a defined threshold value, epsilon in a TFM (e.g., with M rows and N columns) has a value of false (i.e., SAMPLEVALID=false), then the data channel in the output data vector y (which includes neural signal data contributions from that invalid data channel by virtue of its non-zero TFM matrix value) may have its validity flag ELVALID assigned to a value of false (i.e., ELVALID=false). Epsilon may be defined to represent a weight which is small enough as to have an insignificant effect on the output signal (e.g. 0.0001*(1/(M*N)), or the 0.1th percentile of TFM values or weights). This propagation of metadata flags or indicators may be desirable when there are numerous TFM matrix values of zero (i.e., the TFM is sparse), and some combinations of output neural data signals may be usable or valid at least some of the time.

FIGS. 5B-5C depict one example of how a metadata flag that indicates the validity of neural signal data in a data channel may be propagated during processing of that neural signal data. The four recorded neural signal data traces (500) on the left may be linearly transformed by the same TFM (502, 502') into two output neural signal data traces (504a, 504b) on the right. Invalid recorded neural signal data at input signals may be represented by the gray boxed regions (506a, 506b, 506c) on the recorded neural signal data traces (500). When any recorded neural signal data associated with a nonzero weight is invalid, that status information (e.g., in the form of a metadata flag) may be propagated to the transformed output neural signal data traces. The value of this status is represented as gray boxed regions (508a, 508b, 508c) on the output neural signal data traces (504a, 504b). FIG. 5B depicts one example where the matrix value of $W_{1,4}$ is zero. Output data trace (504a) may be composed as a linear combination of input signals X1, X2, X3, and X4. However, because the weight associated with X4 is zero, the invalid status in X4 is not propagated to the output data trace (504a). FIG. 5C depicts one example where the matrix value of $W_{2,1}$ is zero. Output data trace (504b) may be composed as a linear combination of input signals X1, X2, X3, and X4.

However, because the weight associated with X1 is zero, the invalid status in X1 is not propagated to the output data trace (504b).

Methods of Calculating a Transformation Matrix

A transformation matrix TFM may be generated using acquired neural signal data, so that data channels of an input data channel vector corresponding to sensors with valid (and/or usable or relevant data) neural signal data are assigned a non-zero matrix value for one or more output data channels, and data channels corresponding to sensors with invalid (and/or unusable or irrelevant data) are assigned a zero matrix value. Non-zero matrix values may be selected and/or generated and/or identified using iterative methods that iterate through various combinations of matrix values until certain constraints and/or output data channel vector characteristics are met. In some variations, the TFM may be implemented as a bipolar-type matrix (FIG. 6A), a Laplacian-type differential operator (FIG. 6B), and/or a global or local weighted average operator (FIGS. 6C-6D). In some variations, generating a TFM may comprise an automated method that identifies matrix values which satisfy a set of defined constraints as well as possible. These methods may generate the transformation matrix by utilizing neural signal data contained in the data channels recorded by corresponding sensors, tagged segments of the neural signal data, models of the properties of media from which the signals are being recorded, and/or any combination of these or other properties relating to neural characteristics of interest (e.g. correlation between each signal and another signal of interest such as that recorded from a heart rate sensor, correlation between each signal and another measured noise signal such as that recorded from a high impedance voltage sensor near the scalp, signal amplitude in either relevant or irrelevant frequency bands, mutual information measures between groups of signals, etc.). In some variations, matrix values of a TFM may be calculated based on criteria pertaining to the separation of signal data across data channels. Examples of source separation methods may include independent component analysis (ICA), and principal component analysis (PCA) in either its standard form or a modification to favor sparse matrices. In one variation, calculating a TFM may comprise obtaining an intermediate TFM through PCA, multiplying the intermediate TFM with an input data channel vector containing a sample set of neural signal data (e.g., collected during a calibration session), disregarding data channels of the resulting (output) data channel vector having a computed variance at or below a threshold. This threshold may be determined as a multiple of the expected system noise level, a multiple of the expected amplitude of signals of interest, or other methods. A modified version of the input data channel vector may be created by multiplying this modified output data channel vector with the inverse (or pseudo-inverse) of the TFM. Any combination of the above, as well as other approaches may be used to generate the transformation matrix. A TFM may be generated using an external processor (i.e., a processor that is not implanted in a patient), as such computations may utilize processors with computation speeds and/or power demands greater than may be available or tolerated in an implanted processor. In one example, TFM matrix values may be generated using a PCA method comprising normalizing each input data channel by assigning a Z-score, calculating a covariance matrix from the normalized input data channel, obtaining eigenvectors from the covariance matrix using eigen-decomposition, and assigning TFM matrix values to the values of the eigenvectors.

In some examples, system (100) may generate the TFM during a calibration session after the sensors have been implanted in or on brain tissue. For example, after the sensors have been implanted in the brain tissue, the sensors may shift positions within the brain tissue (e.g., in response to trauma to the brain tissue). In response to the shifting (or during the shifting), system (100) may generate the TFM. To this end, system (100) may be configured to detect such shifting of positions of the sensors. This may be performed in any suitable manner.

One variation of generating a TFM may comprise acquiring neural signal data from an implanted device of a neural signal measurement/processing system, transmitting the acquired neural signal data from the implanted device to an external component of the system (e.g., an external processor), generating a TFM using the external processor based on the acquired neural signal data, transmitting the TFM back to the implanted device, and configuring an array of individually addressable logic blocks (e.g., RLMs) to each store a matrix value of the TFM. Optionally, the method may comprise acquiring additional neural signal data and multiplying it with the TFM, and transmitting the TFM-transformed neural signal data to the external component for further processing and analysis. The external component may evaluate the TFM-transformed neural signal data to evaluate whether it contains neural signal data or information of interest, has noise levels or a signal-to-noise ratio within acceptable tolerance ranges, combines data channels with redundant signal data, and/or suppresses data channels with invalid or irrelevant signal data. If so, the measurement system may proceed with the acquisition of neural data and processing the data for transmission using the TFM. If one or more of the desired characteristics for the TFM are not met, the external processor may generate an updated TFM with matrix values by iterating through additional matrix values. The matrix values in a TFM may be determined based on the neural signal data content of each sensor or data channel. For example, a zero matrix value may be assigned to rows of the TFM corresponding to data channels (that map to sensors of the implant) that have been determined to have high levels of noise (e.g., containing a large proportion of spectral content in non-neural frequencies, saturating the rails of an ADC, unstable baseline levels, etc.) and/or containing neural data that does not pertain to a clinical condition or neural region of interest. A non-zero matrix value may be assigned to rows of the TFM corresponding to data channels that have low levels of noise, and/or contain pertinent information (e.g., neural data). Assigning non-zero matrix values across multiple rows along a single column of a TFM may facilitate the combination or compression of input data channels (corresponding to those rows) that have correlated or redundant neural signal data when the input data channel vector is multiplied with the TFM. The non-zero matrix value for each column in a given row of a TFM may be determined based on the desired information content each element or data channel in the output (reduced) data channel vector. For example, the matrix values corresponding to input data channels with a higher signal-to-noise ratio (SNR) may be greater than for input data channels with a lower SNR. Matrix values corresponding to input data channels containing a greater proportion of data or information in a frequency band of interest may be greater than for input data channels that contain a smaller proportion of data or information in the frequency band of interest. Input data channels with independent or non-correlated neural signal data or information may be kept separate from each other by selecting a column of the TFM for each independent data channel, and assigning matrix values of zero for the rows in that particular TFM column that correspond with a different independent data channel. For example, in the case where there are 32 sensors or data channels (M=32) to be linearly combined with a TFM such that the reduced data channel vector has 2 data channels (N=2), the TFM may be a 32×2 matrix. Suppose that input data channels 1-4 contain neural signal data that is independent from input data channels 5-8. In this example, it may be desired that the neural signal data in channels 1-4 is to be combined and represented in the first data channel of the reduced data channel vector (i.e., corresponding to the first column of the TFM) and the neural signal data in channels 5-8 is to be combined and represented in the second data channel of the reduced data channel vector (i.e., corresponding to the second column of the TFM). The resulting TFM may segregate the data or information in channels 1-4 from the data or information in channels 5-8 by assigning matrix values of zero for rows 5-8 in column 1 of the TFM (and optionally, matrix values of zero for rows 9-32 in the same column), and assigning matrix values of zero for rows 1-4 in column 2 of the TFM (and optionally, matrix values of zero for rows 9-32 in the same column). In this fashion, the neural signal data in the first data channel of the reduced data channel vector contains only data or information from channels 1-4 of the input data vector and the second data channel of the reduced data channel vector contains only data or information from channels 5-8 of the input data vector.

In some examples, system (100) may identify data channels with correlated neural signal data. This may be performed in any of the way described herein. For example, system (100) may calculate a correlation coefficient between pairs of data channels and cluster data channels according to the calculated correlation coefficients.

In some examples, system (100) may identify data channels with neural signal data with high levels of noise. This may be performed in any of the way described herein. For example, system (100) may compare a magnitude of predetermined spectral components of neural signal data of the M data channels and identify the data channels that have a magnitude of predetermined spectral components greater than a predetermined threshold value. System (100) may then generate the TFM by assigning a zero value to the matrix values that correspond with the data channels with high levels of noise.

In some examples, system (100) may generate the TEM by identifying valid data channels with neural signal data that have noise levels below a noise threshold, and assigning a non-zero value to the matrix values that correspond with the valid data channels. This may be performed in any of the way described herein. If a data channel contains neural signal data having noise levels that exceed a noise threshold, system (100) may generate a data validity flag for that channel, where the data validity flag indicates that the data channel contains neural signal data having noise levels that exceed the noise threshold.

In some examples, system (100) may generate the TEM by iterating through matrix values such that multiplying the data channel vector with the TFM selects the data channels that have neural signal data pertaining to a neural activity characteristic. The neural activity characteristic may include, for example, a frequency component of the neural signal data (e.g., neural signal data in the beta frequency band (15-30 Hz)).

In some variations, a TFM may be generated (either a new TFM or an updated TFM) when there are any device changes and/or patient parameter changes. For example, the TFM may be updated when lead or sensor migration in neural tissue is detected, sensors are added or removed, acute head injury or perturbation, lead or sensor malfunction, clinical changes in neural state, changing the neural tissue and/or disease of interest, increases or decreases in transmission bandwidth between the implanted components and the external components (i.e., changes in the amount of data compression or reduction), and the like.

Illustrative examples of how a TFM may be tailored to the implantation of a particular instance of a neural signal measurement/processing system, are provided below. In one example, a neural signal measurement/processing system comprising 32 sensors (i.e., 32 recording or data channels) may be implanted in a patient. During the implantation surgery, it may be determined that 1) channels 1-13 are located in a first brain region, 2) channels 14-20 were damaged during the implantation procedure, and 3) channels 21-32 are located in a second brain region that is different from the first brain region. In this example, it may be desirable for the transmission interface between the implanted components and the external components to have sufficient bandwidth to support the transfer of 4 data channels (e.g., two data channels for each the first and second brain regions). In this case, the input data channel vector may comprise 32 elements (M=32) and the desired dimensions of the reduced or output data channel vector may be 4 elements (N=4). The TFM may therefore be a 32×4 matrix. The first two data channels of the reduced data channel vector may consist of the neural data signals from channels 1-13, and the third and fourth data channels of the reduced data channel vector may consist of the neural data signals from channels 21-32. As such, the matrix values for rows 1-13 in the first two columns of the TFM corresponding to each data channel of the input data channel vector may have non-zero values (e.g., the matrix values of rows 21-32 may be zero or smaller than the non-zero values for rows 1-13), and the matrix values for rows 21-32 in the last two columns of the TFM corresponding to each data channel of the input data channel vector may have non-zero values (e.g., the matrix values of rows 1-13 may be zero or smaller than the non-zero values for rows 21-32). Since data channels 14-20 do not have usable or valid data due to sensor damage, the matrix values for rows 14-20 in the TFM may be zero; that is, data channels 14-20 do not contribute to the output or reduced data channel vector. The non-zero matrix values for data channels 1-13 and 21-32 may be determined based on a number of factors, including, but not limited to, neural data signal quality (e.g., low-noise data channels may be assigned a higher matrix value than high-noise data channels), signal type (e.g., data channels containing a higher proportion of data in a frequency-band of interest may assigned a higher matrix value than data channels that have a lower proportion of data in the frequency band of interest), and/or relative locations of the sensors (e.g., data channels corresponding to sensors located at the precise location in the brain region of interest may be assigned a higher matrix value than data channels corresponding to sensors that are located on the periphery of the brain region of interest). In some variations, the non-zero matrix values may have the same magnitude for all data channels of interest, where the data channel in the resultant data channel vector contains an equal portion of neural signal data from all of the data channels of interest.

In another illustrative example, a neural signal measurement/processing system (with optional stimulation hardware and circuitry) comprising 32 sensors (i.e., 32 recording or data channels) may be implanted in a patient approximately near the subthalamic nucleus (STN). In this example, it may be desirable for the transmission interface between the implanted components and the external components to have sufficient bandwidth to support the transfer of 4 data channels (e.g., due to power constraints in the implanted components). The input data channel vector may comprise 32 elements (M=32) and the desired dimensions of the reduced or output data channel vector may be 4 elements (N=4). The TFM may therefore be a 32×4 matrix. Closed-loop deep brain stimulation parameters near the STN may be determined based upon neural activity with frequency components or oscillations in the beta band (about 15 Hz to about 30 Hz), and accordingly, it may be desirable for all four of the data channels of the reduce data channel vector to contain a greater proportion of neural signal data in the beta frequency band. In one variation, 30 minutes of neural activity data may be acquired and recorded from the full 32 channels (i.e., using a TFM that is an identity matrix). The neural activity data may be transmitted to an external processor and configured to train a convolutional neural network (CNN) to generate a 32×4 transformation matrix such that the 4 data channels of the output or reduced data channel vector contain a larger proportion of beta band neural signal data as compared to neural signal data in other frequency bands. The CNN may also calculate matrix values such that the resultant TFM adheres to one or more of the constraints described above. In some variations, a CNN may be trained over a specified length of time (e.g. 120 minutes) using input neural signal data and the desired target features, such as a matrix specifying the desired power spectra of the output signals. The generated TFM may be used to reduce the 32 data channels down to 4 data channels that contain a higher proportion of neural signal data in the beta band. Optionally, if other types of neural signal data are of interest (e.g., neural signal data in other frequency bands, other brain regions, etc.), the external processor may use the CNN with a different set of constraints and training data to calculate a different TFM to tailor the information content of the reduced data channel vector to contain a greater proportion of the neural signal data of interest.

Architecture for Performing Linear Transformation Computations

Figure 7:
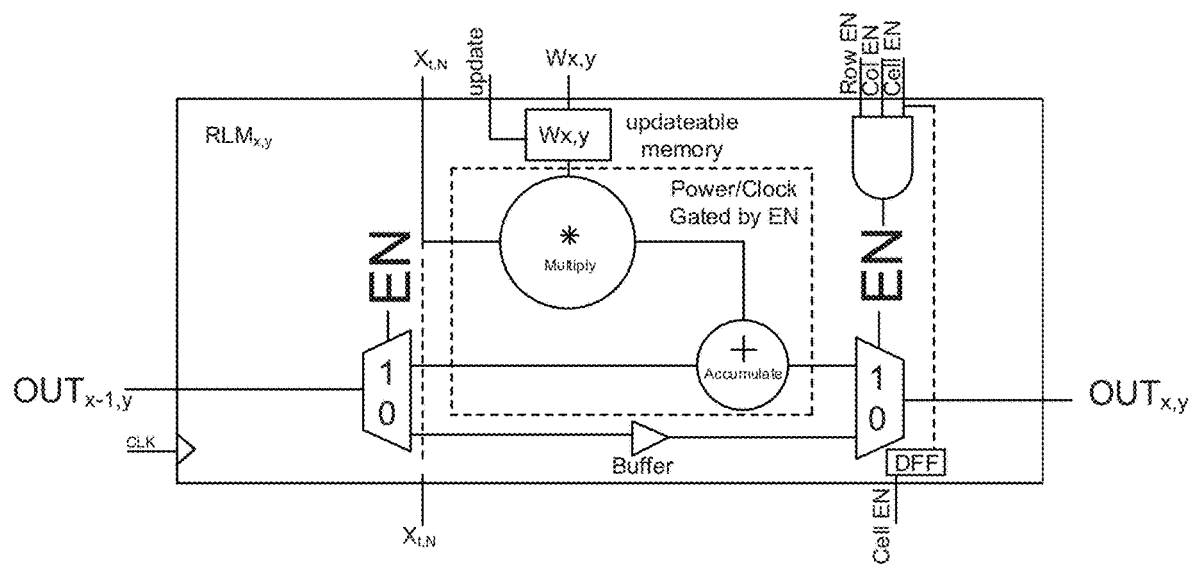
FIG. 7 depicts a functional block diagram of one variation of an individual logic block or RLM, which may be used in a RLM array configured for systolic multiplication.

A transformation matrix may be full or sparse (with differing levels of sparsity), leading to different hardware implementations. Separating channel arrangements that combine recordings taken at different sensor locations or clusters of sensor recording sites may introduce sparsity to a TFM, since many of the matrix values may be zero. Sparsity may also be introduced by the identification of unusable or invalid data channels, where a data channel may be deemed invalid because its corresponding sensor is not connected, not in the desired location, or because it's not operating correctly etc., since the matrix values corresponding to those data channels may also be zero. In one variation, a local processor of an implantable device (e.g., the implantable components of a system of measuring neural signal data) may comprise an array of logic blocks, where the size of the logic block array may be determined at least in part by the array dimensions of the TFM. In some variations, the RLM array size may correspond with the size and number of non-zero matrix values in a TFM. Each logic block may comprise a memory element that may be used to store a non-zero matrix value, one or more computational circuits (e.g., an additional circuit and/or a multiplication circuit), one or more clock input, enable signal input, data input, data output, and/or power inputs. The multiplication of an input data channel vector with a TFM may be carried out in a pipelined fashion, where individual logic blocks or RLMs are sequentially enabled/activated and disabled/deactivated such that the logic blocks that are involved in the immediate computation are enabled and the other logic blocks are disabled. For example, the array of logic blocks or RLMs may be configured for systolic data processing. The enabling and disabling of logic blocks may be controlled by one or more enable signals and/or power signals provided in synchrony with a processor clock signal. FIG. 7 is a functional block diagram of one variation of an individual logic block or RLM, which may be used in a RLM array configured for systolic multiplication. The RLM may be configured to perform a multiplication between the input data value and the updateable transformation matrix value stored in the RLM memory element, then to add the result of that operation with a previous row array element's output value. The RLM may be powered down, either through a row/column shutdown signal, and/or through an enable or power signal. The memory element may be clocked and configured to store the cell-enable value to pass the value down the column. Additionally, the data value may be passed vertically down the array column. Finally, when disabled, a buffer passes through the previous row array cell's output such that in column shutdown scenarios the final value may be sampled from a single output.

In some variations of neural signal acquisition circuitry associated with the sensors (e.g., leads or electrodes), an analog-to-digital converter (ADC) may be connected to each of the sensors and may be used to acquire digitized data for each data channel of an input data channel vector. The ADC may convert sample values at successive channels at small time increments (e.g. 100 μs each) within an overall sample interval (e.g. 100 ms). Within a fraction of the interval, all elements of the data channel vector may be obtained and presented for linear transformation by a TFM. Acquired in this manner, the linear transformation may be carried out by a systolic matrix multiplier, in which a series of multiply and accumulate steps perform the matrix multiplication required. In some variations, a low-power custom hardware architecture may be configured to linearly combine serially-sampled neural channel data with a transformation matrix using a systolic random-logic-macro (RLM) array. The RLM array can be dynamically resized to smaller array dimensions through power and clock gating techniques, which may help reduce the power usage of the processed of the implanted device when multiplying the data channel vector with the TFM. An implantable processor may have a computational architecture that serially samples neural signal data (which may simplify neural signal data insertion into a systolic RLM array), and performs the multiplication of an input data channel vector with a TFM by sequentially activating or enabling a subset of the RLM array to perform intermediate computations of the overall multiplication, and deactivating or disabling RLMs when the intermediate computations are completed. In this fashion, the power consumption of the implantable processor may be reduced, since the computation does not require that all of the RLMs are activated or enabled simultaneously.

In some examples, system (100) may sequentially activate logic blocks and deactivate logic blocks by providing an enable signal to each logic block. In some examples, a high value on the enable signal to a logic block activates the logic block and a low value on the enable signal to a logic block deactivates the logic block.

Optionally, data channel validity flags or indicators may be propagated through an RLM array as well. For example, a flag indicating invalid data may be represented as the most significant bit (MSB) of a data channel, and the MSB may be retained during the multiplication step, and may be combined with the result from the previous cell at an OR operator block during the accumulation step. In this way, any result that was computed using one or more elements of invalid data would itself be marked as invalid.

In some examples, system (100) may generate the TFM if an impedance of an electrode exceeds a pre-determined threshold or if neural signal data measured by the electrodes is outside of an operating range of the ADC. To this end, system (100) may be configured to measure electrode impedance in any suitable manner.

In some examples, system (100) may generate the TFM when the neural signal data is clipped by the ADC. This may be performed in any of the ways described herein.

Figure 8A:
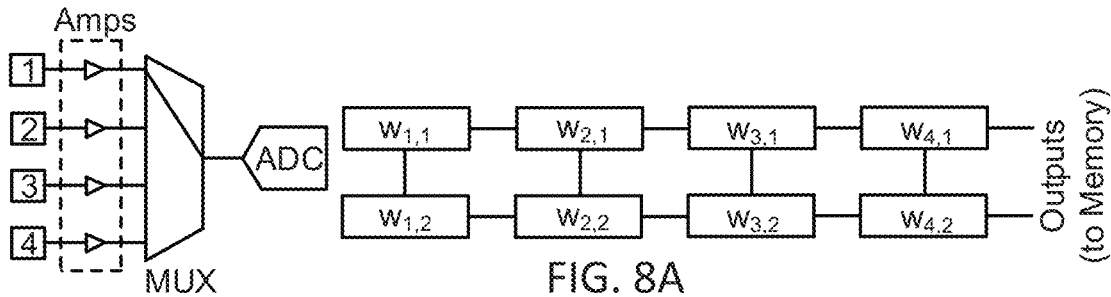
FIGS. 8A-8E depict a schematic representation of one variation of systolic array matrix multiplication.
Figure 8B:
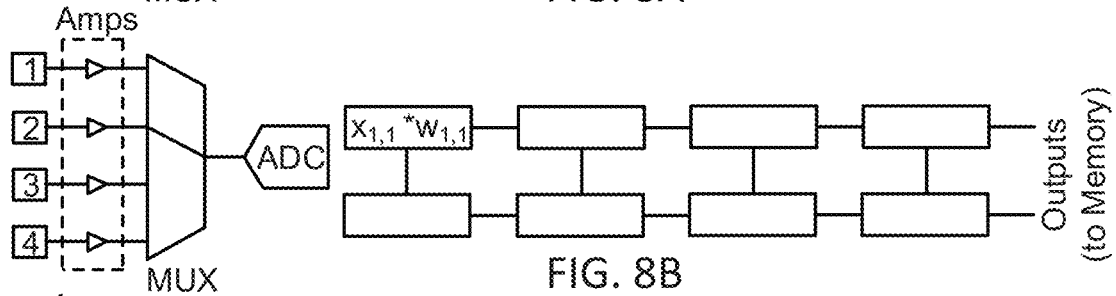
Figure 8C:
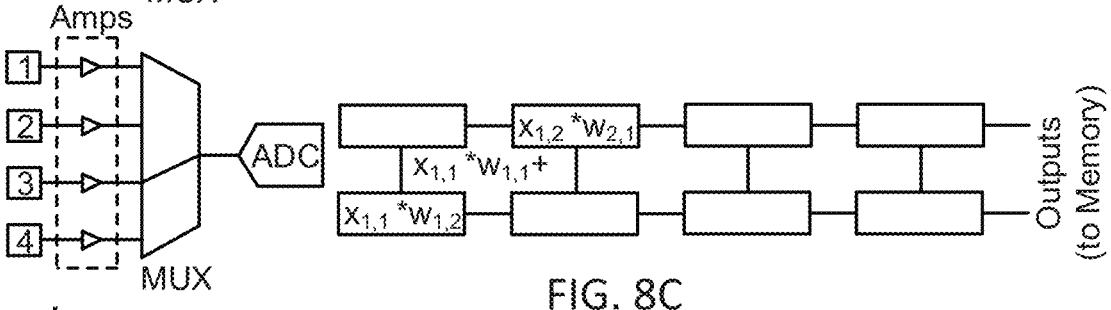
Figure 8D:
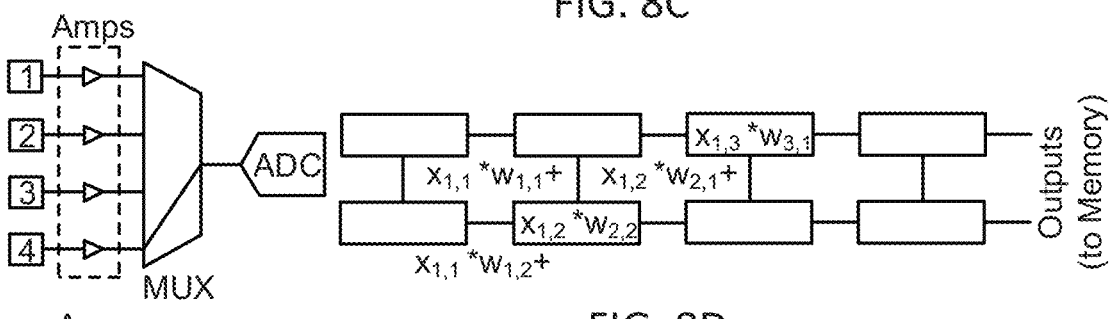
Figure 8E:
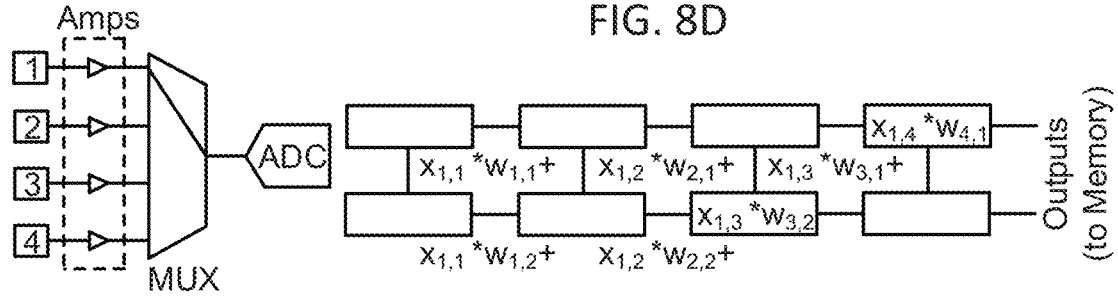
Figure 10A:
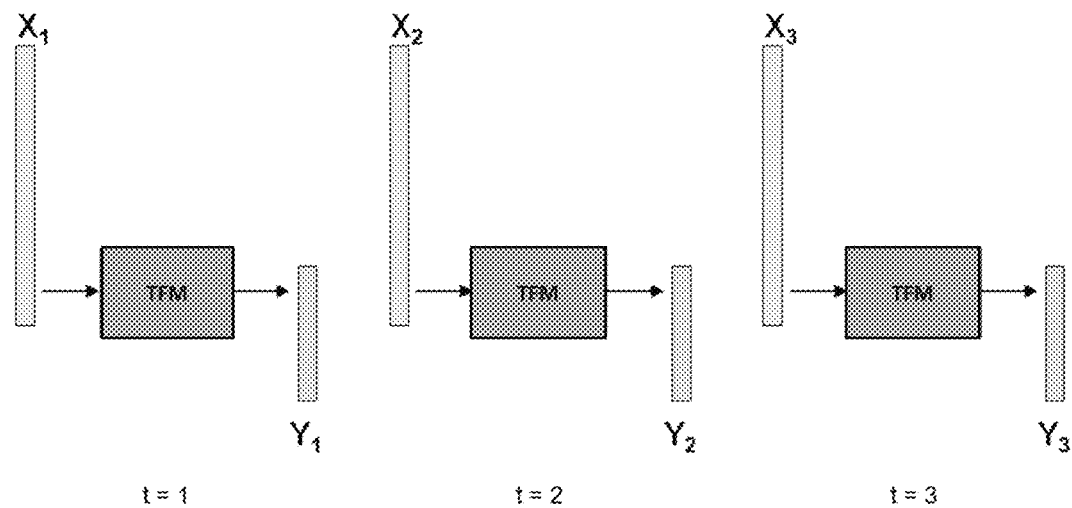
FIGS. 10A-10C depict various hardware architectures and computational methods that may be used for linear transformation of a data channel vector.
Figure 10B:
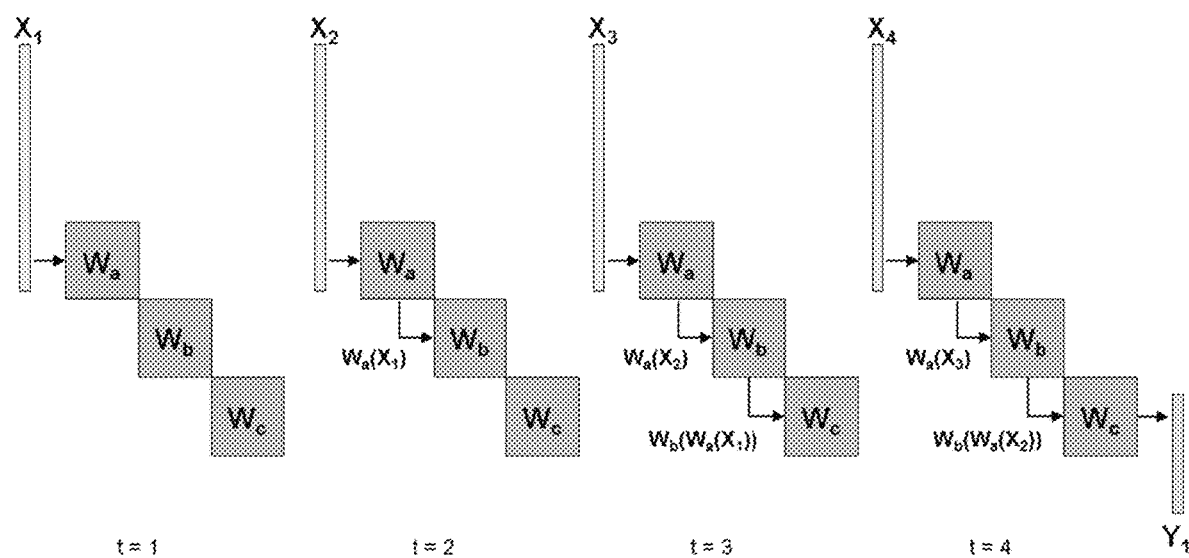
Figure 10C:
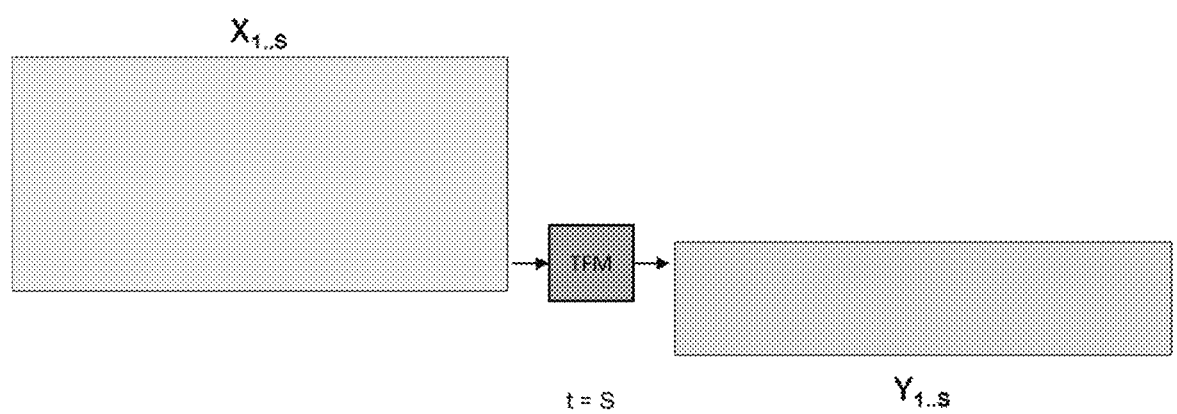

In some variations, a neural signal measurement/processing system may acquire neural signal data sequentially (in an input data channel vector), and may comprise an array of multiply and accumulate logic blocks (e.g., RLMs) that is configured to multiply the input data channel with a TFM the sequentially acquired data in a pipelined fashion. The operation of the systolic array matrix multiplication is depicted in FIGS. 8A-8E. In this example and as depicted in FIG. 8A, neural signal data from four data channels are reduced to a data channel vector with two data channels using a TFM with four columns and two rows. Each RLM of the RLM array may comprise a memory element storing one matrix value of the weight matrix, and each data channel is multiplied with a matrix value and added to a previous value in synchrony with a processor clock signal. On the first clock cycle, as depicted in FIG. 10B, the first sample moves into the upper left RLM of the array. On the next clock cycle, as depicted in FIG. 10C, the same sample is passed to the next RLM in the column unchanged, but is multiplied by the numerical weight stored in the cell and added to the value from the RLM to the left (if any; in this case, there is no RLM to the left, so the output of this multiplication is added to 0). This second RLM to the right takes the second sample of data, as depicted in FIG. 10C, and multiplies the second sample by the RLM's weight value. This is then added to the result from the first RLM, and the result is passed on to the third RLM in the first row. This proceeds until all RLMs have completed their calculations (FIGS. 10D-10E). Additional rows of RLMs beneath the first row follow the same procedure, hence the need to pass the data samples unchanged along the column. This continues until all RLMs have executed the multiplication and addition step.

Feeding the systolic matrix may utilize the nature of the serially sampled neural signal data to populate the elements of the array of RLMs. In some variations, a single ADC may be used to provide serially sampled neural signal data to an entire sensor array. For example, the ADC may be connected through multiplexing to the first recording sensor and performs an analog-to-digital conversion. Upon completion of that conversion, the neural signal data moves to the first RLM in the RLM array. While the second sensor's data is being sampled and converted into the digital domain, the neural signal data from the first sensor may be multiplied by the matrix value of a TFM that is stored within a memory element in the first RLM. This multiplication and the digitization of the second sample may occur simultaneously, which may allow the second RLM in the systolic RLM array to execute its operation. The timing continues to be perfectly aligned as the samples are taken from the sensory array and the elements of the systolic RLM array perform their multiplication and addition function, each subsequent cell receiving data precisely in time to perform the operation. Whenever an RLM completes a computation and is not needed for the next computation cycle, it may be disabled so that it does not consume any power while not actively performing a computation. When all sensors are sampled for a given time step, the process may restart with a second time step. The final calculations from the previous set of samples may finish rippling through the RLM array multiplier, and one full time step worth of data may be stored in memory. Before completion, there may be a delay of d clock cycles, where d is the total number of data channels in an output data channel vector. While other implementations of the systolic matrix multiplier may require special logic to feed data into the matrix multiplier, this form of system eliminates the need for special setup.

Alternatively, multiple ADCs may sample from clusters of sensors such that their incident time delays are always consistent. For instance, in a nine-sensor array, ADC 1 may digitize electrodes 1, 4, and 7, ADC 2 may digitize 2, 5, and 8, and ADC 3 may digitize electrodes 3, 6, and 9. Each ADC may have a set time step delta and therefore, a straightforward amount of delay between its previous incident neural signal data and its next incident neural signal data, which may simplify the setup for feeding neural signal data into the systolic RLM array.

In some variations, the logic blocks or RLMs in an array may be sequentially enabled/activated and disabled/deactivated in a pipelined fashion, where the logic blocks that are involved in the immediate computation are enabled and the other logic blocks are disabled. The activation and deactivation of RLMs may be controlled by an enable signal that may "ripple" across the RLM array to carry out matrix multiplication. Enabling a small subset of elements from the overall array saves static and dynamic power. In the specific example illustrated below, no more than 4 out of 16 RLM instances are enabled/activated at any one time. FIGS. 9A-9H depicts one example of how an enable signal EN percolates across a RLM array in systolic matrix multiplication, where only the blocks that are enabled (i.e., EN=1 or signal high) are activated, while blocks that are not enabled (i.e., EN=0 or signal low) are not activated. This may help to reduce static power and clock loads from presently unused elements within the RLM array. As each individual sample is loaded, its power/clock gating enable is specified by the processor. This enable signal EN may be passed along down the column, with storage in a D flip-flop in the RLM, enabling the subsequent element down the column. This process ensures the subsequent column element is enabled and data is transferred before shutting the current array RLM off. If a systolic RLM array has at most M RLMs, where M is the number of sensors or electrodes, only up to M RLMs may be performing operations at any one time, since only M RLMs are powered/clocked at any given time. This may help reduce the power consumption of the array from (RLM cell power)*M*d (where d is the resulting number of data channels) to (unit RLM power)*M to (unit RLM power) *M+(gated leakage). While other implementations of the systolic multiplication may try to maximally fill the array, this scheme where the RLM array has dimensions matching the dimensions of the RLM, processing serially acquired data in this manner may trade off data throughput for power savings and efficiency. The size of the RLM (e.g., number of RLMs available for processing) may be equal to or greater than the number of leads and/or sensors on the leads, and the size of an RLM array activated for computation may follow the size of the TFM.

While a linear transformation of acquired neural signal data using a TFM may be executed using an array of logic blocks configured for systolic multiplication, in some variations, other hardware architectures and computational methods may be used. In one variation, as each data channel vector is acquired in sequence (i.e., data channel vector $X_1$ acquired at t=1, data channel vector X2 acquired at t=2, data channel vector X3 acquired at t=3, etc.), all of the data channels of the data channel vector may be multiplied by the TFM at once (i.e., complete data channel vector transformation as depicted in FIG. 10A) to obtain output (e.g., reduced) data channel vector Y in sequence. That is, for each sample time-point, the TFM is multiplied by X to produce Y. The TFM transforms input X at a single sample into Y at a single sample. FIG. 10B depicts sequential, pipelined data channel vector transformation. This may be similar to sequential, complete transformation depicted in FIG. 10A, except the transformation takes a number C of cycles to complete. In this case, the data X at a sample time point is fed into a multiplier at each cycle, with the transformation being computed in a pipelined manner (i.e., each TFM matrix value $W_a$, $W_b$, $W_c$ is multiplied with the data channel vector in a pipelined fashion). The TFM transforms input X into Y at a single sample after a fixed number of cycles. After C cycles, Y is produced from X at t=1. After C+1 cycles, Y is produced from X at t=2. In another variation, FIG. 10C depicts frame-based transformation. For a frame interval 1 to S of sample times, the TFM may be multiplied at each sample across every data channel within the entire frame of X, producing output frame Y, which may contain the same number of samples (S) as X. After a number of samples (S) have been buffered, the TFM may transform the complete frame of X (samples $X_1$ to $X_S$) into Y (samples $Y_1$ to $Y_S$).

In some examples, system (100) may display the matrix values of the TFM on a monitor. For example, the matrix values may be displayed on a monitor or other suitable display device of external components (104). This may allow a user to ascertain the matrix values and/or otherwise perform one or more actions based on the matrix values.

Although particular embodiments of the present inventions have been shown and described, it will be understood that it is not intended to limit the present inventions to the disclosed embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

The invention claimed is:

1. A method for detecting neural activity, the method comprising:
    acquiring neural signal data from a plurality of M sensors to generate a data channel vector having M data channels;
    generating a transformation matrix (TFM) comprising an M×N matrix of matrix values, wherein the matrix values are determined by:
        identifying high-noise data channels in the data channel vector with high-noise neural signal data and assigning a zero value to the matrix values in rows of the TFM that correspond to the identified high-noise data channels;
        identifying correlated data channels in the data channel vector that each have correlated neural signal data that is correlated one with neural signal data in one or more other data channels in the data channel vector; and
        iterating through the matrix values of the TFM to compute non-zero matrix values for rows of the TFM that correspond to the identified correlated data channels, wherein the non-zero matrix values of the TFM combine the neural signal data of the correlated data channels; and
    configuring an array of individually addressable logic blocks to have M×N active logic blocks, where each of the addressable logic blocks comprises a memory element that stores a matrix value of the TFM corresponding to each of the addressable logic blocks; and
    generating an output data channel vector having N data elements by multiplying the data channel vector with the TFM using the M×N array of logic blocks.

2. The method of claim 1, further comprising displaying the matrix values of the TFM on a monitor.

3. The method of claim 1, wherein the logic block array is located in an implantable device and wherein the method further comprises transmitting the output data channel vector from the implantable device to an external controller.

4. The method of claim 3, wherein the plurality of M sensors are configured to be attached to the implantable device and are implantable into or in contact with brain tissue, and the data channel vector is configured to be transmitted from the implantable device to a processor of the external controller, and wherein the TFM is generated using the processor of the external controller and transmitted to the implantable device.

5. The method of claim 1, wherein configuring the logic block array comprises providing a gating enable signal to the M×N active logic blocks.

6. The method of claim 1, wherein configuring the logic block array comprises providing a gating enable signal to a number of active logic blocks that correspond with the number of non-zero matrix values of the TFM.

7. The method of claim 1, wherein configuring the logic block array comprises providing a gating power signal to the M×N active logic blocks.

8. The method of claim 1, wherein the identifying of the correlated data channels with the correlated neural signal data comprises calculating a correlation coefficient between pairs of data channels in the data channel vector and clustering the pairs of data channels according to the calculated correlation coefficients.

9. The method of claim 1, wherein the identifying of the high-noise data channels with the high-noise neural signal data comprises comparing a magnitude of predetermined spectral components of the neural signal data of the M data channels and identifying data channels of the M data channels that have a magnitude of predetermined spectral components greater than a predetermined threshold value, and the generating of the TFM comprises assigning the zero value to the matrix values that correspond with the the high-noise data channels.

10. The method of claim 1, wherein generating the TFM further comprises identifying valid data channels with low-noise neural signal data that have noise levels below a noise threshold, and assigning the non-zero value to the matrix values that correspond with the valid data channels.

11. The method of claim 1, wherein generating the TFM further comprises iterating through the matrix values of the TFM such that multiplying the data channel vector with the TFM selects data channels of the M data channels that have neural signal data pertaining to a neural activity characteristic.

12. The method of claim 11, wherein the neural activity characteristic comprises a frequency component of the neural signal data.

13. The method of claim 12, wherein the frequency component comprises neural signal data in the beta frequency band (15-30 Hz).

14. The method of claim 1, further comprising generating a data validity flag for each data channel of the data channel vector indicating whether each data channel contains neural signal data having noise levels that exceed a noise threshold.

15. The method of claim 1, wherein each logic block of the logic block array comprises a multiplication circuit and an addition circuit.

16. The method of claim 15, wherein the logic block array is configured as a systolic matrix multiplier.

17. The method of claim 1, wherein the M sensors comprise M electrodes connected to an analog-to-digital converter (ADC), and the method further comprises generating the TFM if an impedance of an electrode exceeds a pre-determined threshold or if neural signal data measured by the electrodes is outside of an operating range of the ADC.

18. The method of claim 17, wherein the method comprises generating the TFM when the neural signal data is clipped by the ADC.

19. The method of claim 1, wherein the TFM is bipolar-type matrix, a Laplacian-type matrix, a global weighted average matrix, or a local weighted average matrix.

20. The method of claim 1, wherein generating the TFM occurs during a calibration session after the sensors have been implanted in or on brain tissue.

21. The method of claim 1, wherein the sensors are implanted into brain tissue, and generating the TFM occurs when one or more of the plurality of implanted sensors has shifted position within the brain tissue.

22. The method of claim 1, wherein the sensors are implanted into brain tissue, and generating the TFM occurs when trauma to the brain tissue has been detected.

23. The method of claim 1, wherein a first sensor has been implanted into or in contact with a first functional brain region and a second sensor has been implanted into or in contact with a second functional brain region that is different from the first functional brain region.

24. The method of claim 1, further comprising transmitting the output data channel vector to an external controller and reconstructing an approximation of the data channel vector using the external controller by multiplying the output data channel vector with an inverse of the TFM.

25. The method of claim 1, wherein N<M and the output data channel vector is a reduced data channel vector.

26. A method for acquiring and processing neural signal data acquired by a measurement system, the method comprising:
  acquiring neural signal data from a plurality M of sensors in contact with neural tissue, wherein the neural signal data forms a data channel vector having M channel elements;
  multiplying the data channel vector with a M×N transformation matrix (TFM) of data channel values to remove neural signal data redundancies and noise artifacts, wherein the product is a reduced data vector having N data elements, wherein N<=M; and
  transmitting the reduced data vector to an external controller,
  wherein multiplying the data channel vector with the TFM comprises performing systolic matrix multiplication using a logic block array located inside an implanted measurement system controller, wherein the logic block array comprises one logic block per non-zero data channel value of the TFM and each logic block comprises a memory element that stores a non-zero data channel value of the TFM.

27. The method of claim 26, further comprising generating a data validity flag for each data channel of the data channel vector indicating whether a data channel contains neural signal data having noise levels that exceed a noise threshold.

28. The method of claim 27, wherein a data validity flag is generated if the neural signal data corresponds to a malfunctioning activity sensor and/or has signal noise levels that exceed a predetermined noise threshold.

29. The method of claim 26, wherein performing systolic matrix multiplication comprises sequentially activating logic blocks to sequentially multiply data channel values of the TFM with the channel elements of the data channel vector, and sequentially deactivating logic blocks in synchrony with a system clock signal.

* * * * *